US008435984B2

(12) United States Patent
Agarwal et al.

(10) Patent No.: US 8,435,984 B2
(45) Date of Patent: May 7, 2013

(54) TERTIARY AMINE SUBSTITUTED PEPTIDES USEFUL AS INHIBITORS OF HCV REPLICATION

(75) Inventors: Atul Agarwal, Hamden, CT (US); Xiangzhu Wang, Madison, CT (US); Dawei Chen, Middletown, CT (US); Suoming Zhang, Palo Alto, CA (US); Avinash Phadke, Branford, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 382 days.

(21) Appl. No.: 12/597,380

(22) PCT Filed: Feb. 26, 2008

(86) PCT No.: PCT/US2008/002524
§ 371 (c)(1),
(2), (4) Date: May 13, 2010

(87) PCT Pub. No.: WO2008/106130
PCT Pub. Date: Sep. 4, 2008

(65) Prior Publication Data
US 2010/0292219 A1 Nov. 18, 2010

Related U.S. Application Data

(60) Provisional application No. 60/891,634, filed on Feb. 26, 2007.

(51) Int. Cl.
*C07D 401/00* (2006.01)
*C07D 405/00* (2006.01)
*C07D 403/00* (2006.01)
*C07D 217/00* (2006.01)
*A01N 43/40* (2006.01)
*A61K 31/445* (2006.01)
*A61K 31/55* (2006.01)

(52) U.S. Cl.
USPC ........ 514/228.2; 514/323; 540/602; 544/373; 546/147; 546/200; 548/517

(58) Field of Classification Search .................. None
See application file for complete search history.

(56) References Cited

U.S. PATENT DOCUMENTS

| 6,872,805 | B2 | 3/2005 | Campbell et al. |
| 6,908,901 | B2 | 6/2005 | Bailey et al. |
| 6,995,174 | B2 * | 2/2006 | Wang et al. .................. 514/312 |
| 7,041,698 | B2 | 5/2006 | Ripka et al. |
| 7,176,208 | B2 | 2/2007 | Nakajima et al. |
| 7,906,619 | B2 | 3/2011 | Phadke et al. |
| 2003/0224977 | A1 | 12/2003 | Llinas-Brunet et al. |
| 2004/0002448 | A1 | 1/2004 | Tsantrizos et al. |
| 2004/0048802 | A1 | 3/2004 | Ripka et al. |
| 2004/0077551 | A1 | 4/2004 | Campbell et al. |
| 2004/0106559 | A1 | 6/2004 | Wang et al. |
| 2004/0224900 | A1 | 11/2004 | Bailey et al. |
| 2005/0020503 | A1 | 1/2005 | Llinas-Brunet et al. |
| 2005/0153877 | A1 | 7/2005 | Miao et al. |
| 2005/0267040 | A1 | 12/2005 | Scola et al. |
| 2006/0019905 | A1 | 1/2006 | Bailey et al. |
| 2006/0046965 | A1 | 3/2006 | Bailey et al. |
| 2006/0046983 | A1 | 3/2006 | Hudyma et al. |
| 2006/0142204 | A1 | 6/2006 | Halfon et al. |
| 2006/0199773 | A1 | 9/2006 | Sausker et al. |
| 2006/0281688 | A1 | 12/2006 | Zhang et al. |
| 2007/0010455 | A1 | 1/2007 | Hewawasam et al. |
| 2007/0093414 | A1 | 4/2007 | Carini et al. |
| 2007/0099825 | A1 | 5/2007 | D'Andrea et al. |
| 2009/0048297 | A1 | 2/2009 | Phadke et al. |
| 2010/0216725 | A1 | 8/2010 | Phadke et al. |

FOREIGN PATENT DOCUMENTS

| WO | 0059929 A1 | 10/2000 |
| WO | 02060926 A2 | 8/2002 |
| WO | 03099274 A1 | 12/2003 |
| WO | 03099316 A1 | 12/2003 |
| WO | 2004043339 A2 | 5/2004 |
| WO | 2004072243 A2 | 8/2004 |
| WO | 2004094452 A2 | 11/2004 |
| WO | 2004103996 A1 | 12/2004 |
| WO | 2004113365 A2 | 12/2004 |
| WO | 2005028501 A1 | 3/2005 |
| WO | 2005037214 A2 | 4/2005 |
| WO | 2005046712 A1 | 5/2005 |
| WO | 2005051410 A1 | 6/2005 |
| WO | 2005054430 A2 | 6/2005 |
| WO | 2005070955 A1 | 8/2005 |
| WO | 2005073216 A2 | 8/2005 |

(Continued)

OTHER PUBLICATIONS

Andrews, et al., "Pyrrolidine-5,5-trans-lactams. 2. The Use of X-ray Crystal Structure Data in the Optimization of P3 and P4 Substituents," Organic Letters, 4(25): 4479-4482 (2002).
Arasappan, et al., "Hepatitis C virus NS3-4A serine protease inhibitors: SAR of P2 moiety with improved potency," Bioorganic & Medicinal Chemistry Letters, 15: 4180-4184 (2005).
Barbato, et al., "Inhibitor binding induces active site stabilization of the HCV NS3 protein serine protease domain," The EMBO Journal, 19(6): 1195-1206 (2000).
Di Marco, et al., "Inhibition of the Hepatitis C Virus NS3/4A Protease," The Journal of Biological Chemistry, 275(10): 7152-7157 (2000).
International Search Report for Application No. PCT/US2007/016018 dated Dec. 12, 2007.
Lin, et al., "In Vitro Resistance Studies of Hepatitis C Virus Serine Protease Inhibitors, VX-950 and BILN 2061," The Journal of Biological Chemistry 279(17): 17508-17514 (2004).
Liu, et al., "Hepatitis C NS3 protease inhibition by peptidyl-alpha-ketoamide inhibitors: kinetic mechanism and structure," Archives of Biochemistry and Biophysics, 421: 207-216 (2004).
Llinas-Brunet, et al., "A Systematic Approach to the Optimization of Substrate-Based Inhibitors of the Hepatitis C Virus NS3 Protease: Discovery of Potent and Specific Tripeptide Inhibitors," J. Med. Chem., 47: 6584-6594 (2004).
Ontoria, et al., "The Design and Enzyme-Bound Crystal Structure of Indoline Based Peptidomimetic Inhibitors of Hepatitis C Virus NS3 Protease," J. Med. Chem., 47: 6443-6446 (2004).

(Continued)

*Primary Examiner* — Anna Pagonakis
(74) *Attorney, Agent, or Firm* — Cantor Colburn LLP

(57) ABSTRACT

The present invention provides tertiary amine substituted peptides of Formula (I) useful as inhibitors of HCV replication. The variables R and $R_1$-$R_{12}$ in Formula I are described herein. The invention also includes methods for preparing such compounds. The present invention further includes pharmaceutical compositions containing tertiary amine substituted peptides and methods for using such compounds, including methods for using the compounds to treat hepatitis C infection.

22 Claims, No Drawings

FOREIGN PATENT DOCUMENTS

| | | | |
|---|---|---|---|
| WO | 2005090383 | A2 | 9/2005 |
| WO | 2005095403 | A2 | 10/2005 |
| WO | 2006007700 | A1 | 1/2006 |
| WO | 2006007708 | A1 | 1/2006 |
| WO | 2006002076 | A2 | 2/2006 |
| WO | 2006033878 | A1 | 3/2006 |
| WO | 2006086381 | A2 | 8/2006 |
| WO | 2006096652 | A2 | 9/2006 |
| WO | 2007005838 | A2 | 1/2007 |
| WO | 2007009227 | A1 | 1/2007 |
| WO | 2007025307 | A2 | 3/2007 |
| WO | 2007030656 | A1 | 3/2007 |
| WO | 2007044893 | A2 | 4/2007 |
| WO | 2008095058 | A1 | 8/2008 |

OTHER PUBLICATIONS

Tsantrizos, et al., "Macrocyclic Inhibitors of the NS3 Protease as Potential Therapeutic Agents of Hepatitis C Virus Infection," Agnew. Chem. Int. Ed., 42(12): (2003).

Venkatraman, et al., "Discovery of (1R,5S)-N-[3-Amino-1-(cyclobutylmethyl)-2,3-dioxopropyl]-3-[2(S)-[[[(1,1-dimethylethyl)amino}amino]-3,3-dimethyl-1-oxobutyl]-6,6-dimethyl-3-azabicyclo[3.1.0]hexan-2(S)-carboxamide (SCH 503034), a Selective, Potent, Orally Bioavailable Hepatitis C Virus NS3 Protease Inhibitor: A Potential Therapeutic Agent for the Treatment of Hepatitis C Infection," J. Med. Chem., 49: 6074-6086 (2006).

European Supplemental Search Report for EU Application No. 09832541.8, International Filing Date: Jun. 17, 2010, Date of Mailing: Jul. 27, 2012. 6 Pages.

Rakic, et al., "A Small-Molecule Probe for Hepatitis C Virus Replication that Blocks Protein Folding," Chemistry & Biology, 13: 1051-1060 (2006).

Extended European Search Report, U.S. Appl. No. 12/164,823, Date of Mailing Jul. 17, 2012, 15 Pages.

Slater, et al., "Pyrrolidine-5,5-trans-lactams. 4. Incorporation of a P3/P4 Urea Leads to Potent Intracellular Inhibitors of Hepatitis C Virus NS3/4A Protease," Organic Letters, (2003) 5(24): 4627-4630.

European Written Opinion for European Application No. 07810457, European Filing Date: Oct. 12, 2011; Date of Mailing: Sep. 27, 2012, 4 Pages.

Slater, et al., "Pyrrolidine-5,5-trans-lactams. 4. Incorporation of a P3/P4 Urea Leads to Potent Intracellular Inhibitors of Hepatitis C Virus NS3/4A Protease," Organic Letters, 5(24): 4627-4630 (2003).

* cited by examiner

TERTIARY AMINE SUBSTITUTED PEPTIDES USEFUL AS INHIBITORS OF HCV REPLICATION

This application is a U.S. National Stage application filed under 35 U.S.C. §371 from PCT/US2008/002524 filed 26 Feb. 2008 which is a PCT application of U.S. Provisional 60/891,634, filed Feb. 26, 2007, which is hereby incorporated by reference in its entirety.

FIELD OF INVENTION

The present invention provides tertiary amine substituted peptides useful as inhibitors of HCV replication. The invention also includes methods for preparing such compounds. The present invention further includes pharmaceutical compositions containing tertiary amine substituted peptides and methods for using such compounds, including methods for using the compounds to treat hepatitis C infection.

BACKGROUND

An estimated 3% of the world's population is infected with the hepatitis C virus. Of those exposed to HCV, 80% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will clear HCV.

HCV is an enveloped, single-stranded RNA virus that contains a positive-stranded genome of about 9.6 kb. HCV is classified as a member of the *Hepacivirus* genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

NH2-C-E1-E2-p7-NS2-NS3-NS4A-NS4B—NS5A-NS5B—COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B—NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. Provisional application 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Direct acting antiviral agents such as VX-950 and NM 283 (prodrug of NM 107) are in clinical development for treatment of chronic HCV. Due to lack of effective therapies for treatment for certain HCV strains and the high mutation rate of HCV, new therapies are needed. The present invention fulfills this need and provides additional advantages, which are described herein.

SUMMARY OF INVENTION

Compounds useful for treating and preventing hepatitis C infections, pharmaceutical compositions, and methods for use of such compounds are provided herein.

In one aspect, the present invention includes compounds of Formula I and pharmaceutically acceptable salts thereof.

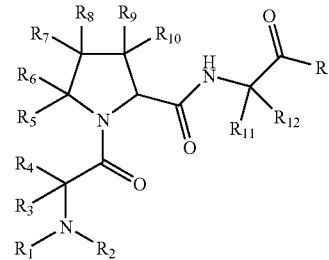

Formula I

Within Formula I the variables R and $R_1$-$R_{12}$ carry the definitions set forth below.

R is hydroxyl, $C_1$-$C_4$alkoxy,

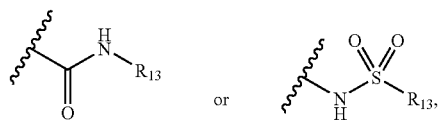

or where $R_{13}$ is defined herein.

$R_1$ is $C_1$-$C_6$alkyl, $C_2$-$C_6$alkenyl, $C_3$-$C_7$cycloalkyl, phenyl, heterocycloalkyl, or 5- or 6-membered heteroaryl, each of which is optionally substituted.

$R_2$ is $C_1$-$C_6$ alkyl or $C_2$-$C_6$alkenyl; each of which is optionally substituted.

Or, $R_1$ and $R_2$ are joined to form a 5- to 7-membered heterocycloalkyl ring containing 0, 1, or 2 additional heteroatoms independently chosen from O, N, or S, which ring is substituted with 0 or 1 or more substituents independently chosen from halogen, hydroxyl, $C_1$-$C_4$alkyl, $C_1$-$C_4$alkoxy, oxo, $C_1$-$C_2$haloalkyl, and $C_1$-$C_2$haloalkoxy.

$R_3$ and $R_{11}$ are independently $C_1$-$C_6$alkyl, $C_2$-$C_6$alkenyl, $C_2$-$C_6$alkanoyl, or mono- or di-$C_1$-$C_6$alkylamino, ($C_3$-$C_7$cycloalkyl)$C_0$-$C_4$alkyl, ($C_3$-$C_7$cycloalkenyl)$C_0$-$C_4$alkyl, (phenyl)$C_0$-$C_2$alkyl, or (heterocycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

$R_4$ and $R_{12}$ are independently hydrogen, halogen, hydroxyl, amino, $C_1$-$C_6$alkyl, $C_2$-$C_6$alkenyl, or $C_1$-$C_6$alkoxy.

Or, $R_3$ and $R_4$ are be joined to form a 3- to 7-membered cycloalkyl ring or 5- to 7-membered heterocycloalkyl ring, each of which is substituted with 0 to 2 substituents independently chosen from halogen, hydroxyl, amino, cyano, vinyl, $C_1$-$C_2$alkyl, $C_1$-$C_2$alkoxy, trifluoromethyl, and trifluoromethoxy.

Or, $R_{11}$ and $R_{12}$ are be joined to form a 3- to 7-membered cycloalkyl ring or 5- to 7-membered heterocycloalkyl ring, each of which is substituted with 0 to 2 substituents independently chosen from halogen, hydroxyl, amino, cyano, vinyl, $C_1$-$C_2$alkyl, $C_1$-$C_2$alkoxy, trifluoromethyl, and trifluoromethoxy.

Or, $R_3$ is a $C_7$-$C_{11}$ saturated or unsaturated hydrocarbon chain that is (i) covalently bound to $R_{11}$, where $R_{11}$ is a methylene group or (ii) covalently bound to a cycloalkyl group formed by $R_{11}$ and $R_{12}$ being joined to from a 3- to 7-membered cycloalkyl ring.

$R_5$, $R_6$, $R_7$, and $R_{10}$ are independently hydrogen, halogen, cyano, amino, hydroxyl, $C_1$-$C_2$alkyl, $C_1$-$C_2$alkoxy, $C_1$-$C_2$haloalkyl, or $C_1$-$C_2$haloalkoxy.

$R_8$ is a group of the formula —$(CH_2)_n Y$—Z, where n is 0, 1, or 2, and $R_9$ is hydrogen, halogen, amino, $C_1$-$C_2$alkyl, or $C_1$-$C_2$alkoxy; $R_8$ and $R_9$ are taken together to form an optionally substituted 5- to 7-membered cycloalkyl ring.

$R_{13}$ is $C_1$-$C_6$alkyl, $C_2$-$C_6$alkenyl, each of which is substituted with 0 or 1 or more substituents independently chosen from halogen, hydroxyl, amino, cyano, amino, $C_1$-$C_4$alkoxy, mono or di-$C_1$-$C_4$alkylamino.

Or, $R_{13}$ is ($C_3$-$C_7$cycloalkyl)$C_0$-$C_2$alkyl, (aryl)$C_0$-$C_2$alkyl, (5- to 7-membered heterocycloalkyl)$C_0$-$C_2$alkyl, or (heteroaryl)$C_0$-$C_2$alkyl, each of which is substituted with 0 or 1 or more substituents independently chosen from halogen, hydroxyl, amino, cyano, amino, $C_1$-$C_4$alkyl, $C_1$-$C_4$alkoxy, mono or di-$C_1$-$C_4$alkylamino, $C_1$-$C_2$haloalkyl, or $C_1$-$C_2$haloalkoxy.

Y is absent, $CR_{14}R_{15}$, $NR_{16}$, S, —O—, —O(C=O)$(NR_{16})$—, —$OC_{14}R_{15}$—, NH(C=O)$(NR_{16})$—, —$NR_{16}$(C=O)$CR_{14}R_{15}$—, NH(S=O)$(NR_{16})$—, or —O(C=O)—.

Wherein $R_{14}$ and $R_{15}$ are independently hydrogen, hydroxyl, halogen, $C_1$-$C_2$alkyl, $C_1$-$C_2$alkoxy, $C_1$-$C_2$haloalkyl, or $C_1$-$C_2$haloalkoxy, and $R_{16}$ is hydrogen, $C_1$-$C_2$alkyl, $C_1$-$C_2$haloalkyl, or $C_1$-$C_2$haloalkoxy.

Z is $C_1$-$C_6$alkyl, $C_2$-$C_6$alkenyl, (mono- or bicyclic aryl)$C_0$-$C_2$alkyl, (mono- or bicyclic heteroaryl)$C_0$-$C_2$alkyl, ($C_3$-$C_7$cycloalkyl)$C_0$-$C_2$alkyl, (5- or 6-membered heterocycloalkyl)$C_0$-$C_2$alkyl, partially unsaturated bicyclic heterocycle, tricyclic aryl, or tricyclic heteroaryl; each of which Z is substituted with 0 or more substituents independently chosen from halogen, hydroxyl, amino, cyano, —$CONH_2$, —COOH, mono- and di-$C_1$-$C_4$alkylsulfonamide, mono- and di-$C_1$-$C_4$alkylcarboxamide, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy, and 0 or 1 ($C_3$-$C_7$cycloalkyl)$C_0$-$C_2$alkyl, (aryl)$C_0$-$C_2$alkyl, (phenyl)$C_0$-$C_2$alkoxy, (5- or 6-membered heteroaryl)$C_0$-$C_2$alkyl, (5- or 6-membered heterocycloalkyl)$C_0$-$C_2$alkoxy, indanyl, (5- or 6-membered heterocycloalkyl)$C_0$-$C_2$alkyl, or 9- or 10 membered bicyclic heteroaryl, each of which is substituted with 0, 1, or 2 substituents independently chosen from (a) and 0 or 1 substituents (b).

Where (a) is chosen from halogen, hydroxyl, amino, cyano, nitro, —COOH, —$CONH_2$, NOH, $C_1$-$C_4$alkyl, $C_1$-$C_4$alkoxy, $C_2$-$C_4$alkanoyl, $C_1$-$C_4$hydroxyalkyl, mono- and di-$C_1$-$C_4$alkylamino, $C_1$-$C_4$alkylester, mono- and di-$C_1$-$C_4$alkylsulfonamide, mono- and di-$C_1$-$C_4$alkylcarboxamide, $C_1$-$C_2$haloalkyl, $C_1$-$C_2$haloalkoxy, and (b) is phenyl and 5- or 6-membered heteroaryl, each of which is substituted with 0 or 1 or more substituents independently chosen from halogen, hydroxyl, amino, —CHO, —COOH, —NH(C=O)H, $C_1$-$C_4$alkyl, $C_1$-$C_2$alkoxy, mono- and di-($C_1$-$C_4$alkyl)amino, mono-and di-($C_1$-$C_4$alkyl)carboxamide, $C_1$-$C_4$alkylester, ($C_1$-$C_4$alkylester)amino, $C_1$-$C_2$haloalkyl, and $C_1$-$C_2$haloalkoxy.

The invention includes pharmaceutical compositions comprising a compound of the invention or a salt thereof, containing at least one pharmaceutically acceptable carrier. The invention also includes pharmaceutical compositions comprising a compound of the invention and containing at least one additional active agent. The invention includes packaged pharmaceutical compositions comprising a compound of the invention in a container and further comprising instructions for using the composition to treat a patient infected with a hepatitis C virus or susceptible to infection with a hepatitis C virus.

In another aspect the invention provides a method for treating or preventing hepatitis C infection comprising providing an effective amount of a compound or salt of the invention to a patient in need of such treatment or prevention.

A method of inhibiting HCV replication in vivo comprising administering to a patient infected with HCV a concentration of a compound or salt of the invention sufficient to inhibit HCV replicon replication in vitro is also included in the invention.

These and other aspects of the invention will be more clearly understood with reference to the following detailed description, examples and claims.

DETAILED DESCRIPTION

Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

Formula I includes all subformulae thereof. For example Formula I includes compounds of Formulas I-IX and the pharmaceutically acceptable salts, prodrugs, hydrates, polymorphs, and thereof.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound of Formula I), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

In certain situations, the compounds of Formula I may contain one or more asymmetric elements such as stereogenic centers, including chiral centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Formula I includes all chiral forms, stereoisomers, diastereomers, and enantiomers of compounds of Formula I.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Where a compound exists in various tautomeric forms, the invention is not limited to any one of the specific tautomers, but rather includes all tautomeric forms.

The invention includes compounds of Formula I having all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. R, $R_1$-$R_{12}$, Y and Z. Unless otherwise specified, each variable within Formula I is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —(CH$_2$)C$_3$-C$_7$cycloalkyl is attached through carbon of the methylene (CH$_2$) group.

"Alkyl" includes both branched and straight chain saturated aliphatic hydrocarbon groups, having the specified number of carbon atoms, generally from 1 to about 12 carbon atoms. The term C$_1$-C$_6$alkyl as used herein indicates an alkyl group having from 1 to about 6 carbon atoms. When C$_0$-C$_n$ alkyl is used herein in conjunction with another group, for example, (phenyl)C$_0$-C$_4$ alkyl, the indicated group, in this case phenyl, is either directly bound by a single covalent bond (C$_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkanoyl" is an alkyl group as defined above, attached through a keto (—(C=O)—) bridge. Alkanoyl groups have the indicated number of carbon atoms, with the carbon of the keto group being included in the numbered carbon atoms. For example a C$_2$alkanoyl group is an acetyl group having the formula CH$_3$(C=O)—.

"Alkenyl" means straight and branched hydrocarbon chains comprising one or more unsaturated carbon-carbon bonds, which may occur in any stable point along the chain. Alkenyl groups described herein typically have from 2 to about 12 carbons atoms. Preferred alkenyl groups are lower alkenyl groups, those alkenyl groups having from 2 to about 8 carbon atoms, e.g. C$_2$-C$_8$, C$_2$-C$_6$, and C$_2$-C$_4$ alkenyl groups. Examples of alkenyl groups include ethenyl, propenyl, and butenyl groups.

"Alkoxy" means an alkyl group, as defined above, with the indicated number of carbon atoms attached via an oxygen bridge. Examples of alkoxy include, but are not limited to, methoxy, ethoxy, 3-hexoxy, and 3-methylpentoxy.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

"Alkylester" indicates an alkyl group as defined above attached through an ester linkage. The ester linkage may be in either orientation, e.g. a group of the formula —O(C=O) alkyl or a group of the formula —(C=O)Oalkyl.

"Alkylthio" indicates an alkyl group as defined above attached through a sulfur linkage, i.e. a group of the formula alkyl-S—. Examples include ethylthio and pentylthio.

"Aryl" means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Bicyclic aryl groups may contain two fused aromatic rings (naphthyl) or an aromatic ring fused to a 5- to 7-membered non-aromatic cyclic group that optionally contains 1 or 2 heteroatoms independently chosen from N, O, and S, for example, a 3,4-methylenedioxyphenyl group. Aryl groups include, for example, phenyl, naphthyl, including 1-naphthyl and 2-naphthyl, and bi-phenyl.

"Mono- and/or di-alkylcarboxamide" indicates groups of formula (alkyl$_1$)—NH—(C=O)— and (alkyl$_1$)(alkyl$_2$)—N—(C=O)— in which the alkyl$_s$ and alkyl$_2$ groups are independently chosen alkyl groups as defined above having the indicated number of carbon atoms. Mono and/or di-alkylcarboxamide also refers to groups of the formula —NH(C=O)(alkyl$_1$) and —N(alkyl$_2$)(C=O)(alkyl$_1$), carboxamide groups in which the point of attachment is the nitrogen atom, in which the alkyl$_1$ and alkyl$_2$ groups are independently chosen alkyl groups as defined above having the indicated number of carbon atoms.

"Mono- and di-alkylsulfonamide" means groups of the formula (alkyl$_1$)—NH—(SO$_2$)— and (alkyl$_1$)(alkyl$_2$)—N—(SO$_2$)— in which the alkyl$_1$ and alkyl$_2$ groups are independently chosen alkyl groups as defined above having the indicated number of carbon atoms. Mono and/or di-alkylcarboxamide also refers to groups of the formula —NH(SO$_2$)(alkyl$_1$) and —N(alkyl$_2$)(SO$_2$)(alkyl$_1$), sulfonamide groups in which the point of attachment is the nitrogen atom, in which the alkyl$_1$ and alkyl$_2$ groups are independently chosen alkyl groups as defined above having the indicated number of carbon atoms.

"Cycloalkyl" indicates a saturated hydrocarbon ring group, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane. (Cycloalkyl)C$_0$-C$_2$alkyl means a cycloalkyl group as defined above attached to the core group it substitutes via a single covalent bond (C$_0$alkyl) or via a methylene or ethylene linker.

"Cycloalkenyl" as used herein, means an unsaturated, but not aromatic, hydrocarbon ring having at least one carbon-carbon double bond. Cycloalkenyl groups contain from 4 to about 8 carbon atoms, usually from 4 to about 7 carbon atoms. Examples include cyclohexenyl and cyclobutenyl. In the term "(cycloalkenyl)alkyl" the terms "cycloalkenyl" and "alkyl" are as defined above, and the point of attachment is on the alkyl group.

"Mono- or bicyclic heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. In certain embodiments 5- to 6-membered heteroaryl groups are preferred. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Heterocycloalkyl" means a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized. A (heterocycloalkyl)$C_0$-$C_2$alkyl means a heterocycloalkyl group as defined above attached to the core group it substitutes via a single covalent bond ($C_0$alkyl) or via a methylene or ethylene linker.

"Haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge (oxygen of an alcohol radical).

"Halo" or "halogen" as used herein refers to fluoro, chloro, bromo, or iodo.

"Hydroxyalkyl" is an alkyl group as defined herein substituted with at least on hydroxyl substituent.

The phrase "optionally substituted" indicates that such groups may either be unsubstituted or substituted at one or more of any of the available positions, typically 1, 2, 3, or 4 positions, by one or more suitable groups such as those disclosed herein.

The phrase Suitable groups that may be present on an "optionally substituted" position include, but are not limited to, e.g., halogen, cyano, hydroxyl, amino, nitro, oxo, azido, alkanoyl (such as a $C_2$-$C_6$ alkanoyl group such as acyl or the like); carboxamido; alkylcarboxamide; alkylester groups; alkyl groups, alkoxy groups, alkylthio groups including those having one or more thioether linkages, alkylsulfinyl groups including those having one or more sulfinyl linkages, alkylsulfonyl groups including those having one or more sulfonyl linkages, mono- and di-aminoalkyl groups including groups having one or more N atoms, all of the foregoing optional alkyl substituents may have one or more methylene group replaced by an oxygen or —NH—, and have from about 1 to about 8, from about 1 to about 6, or from 1 to about 4 carbon atoms, cycloalkyl; phenyl; phenylalkyl with benzyl being an exemplary phenylalkyl group, phenylalkoxy with benzyloxy being an exemplary phenylalkoxy group; a saturated, unsaturated, or aromatic heterocyclic groups having 1 ring and one or more N, O or S atoms, e.g. pyridyl, pyrazinyl, pyrimidinyl, furanyl, pyrrolyl, thienyl, thiazolyl, triazinyl, oxazolyl, isoxazolyl, imidazolyl, tetrahydrofuranyl, tetrahydropyranyl, piperidinyl, morpholinyl, piperazinyl, and pyrrolidinyl. Any such groups having additional positions available for substitution may be further substituted, e.g with substituents independently chosen from, e.g., amino, hydroxyl, alkyl, alkoxy, halogen, haloalkyl, haloalkoxy, and mono- and di-alkylamino.

"Pharmaceutical compositions" are compositions comprising at least one active agent, such as a compound or salt of Formula I, and at least one other substance, such as a carrier, excipient, or diluent. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COON where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions of the invention refers to a diluent, excipient, or vehicle with which an active compound is administered.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Prodrug" means any compound that becomes compound of the invention when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of the invention.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment," as used herein includes providing a compound of Formula I and at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of Formula I and at least one additional active agent to a patient having or susceptible to a hepatitis C infection.

A "therapeutically effective amount" of a pharmaceutical combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roch TaqMan assay. In certain preferred embodiments treatment reduces HCV RNA levels below the limit of quantitation (30 IU/mL, as measured by the Roche TaqMan® assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where p<0.05.

Chemical Description

The invention includes compounds of Formula I, as discussed above. Additionally the invention includes, as alternate embodiments, compound and salts of Formula I in which the variables A and $R_3$-$R_7$ carry the values set forth below.

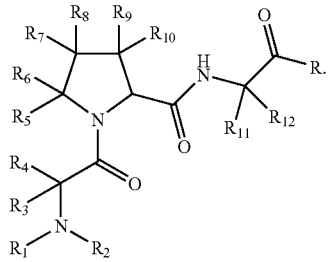

Formula I

The $R_1$ and $R_2$ Variables (a) $R_1$ is $C_1$-$C_6$alkyl, $C_2$-$C_6$alkenyl, $C_3$-$C_7$cycloalkyl, phenyl, heterocycloalkyl, or 5- or 6-membered heteroaryl, each of which is optionally substituted; and $R_2$ is $C_1$-$C_6$ alkyl or $C_2$-$C_6$alkenyl; each of which is optionally substituted.

(b) $R_1$ and $R_2$ are joined to form a 5- to 7-membered heterocycloalkyl ring, which ring is substituted with 0 or 1 or more substituents independently chosen from halogen, hydroxyl, $C_1$-$C_4$alkyl, $C_1$-$C_4$alkoxy, $C_1$-$C_2$haloalkyl, and $C_1$-$C_2$haloalkoxy.

(c) $R_1$ and $R_2$ are joined to form a pyrrolidinyl, piperidinyl, or piperazinyl ring, each of which is substituted with 0, 1, or 2 substituents independently chosen from halogen, hydroxyl, $C_1$-$C_2$alkyl, $C_1$-$C_2$alkoxy, trifluoromethyl, and trifluoromethoxy.

The $R_3$, $R_4$, $R_{11}$, and $R_{12}$ Variables (d) $R_3$ is $C_1$-$C_6$alkyl, $C_2$-$C_6$alkenyl, $C_2$-$C_6$alkanoyl, or mono- or di-$C_1$-$C_6$alkylamino, ($C_3$-$C_7$cycloalkyl)$C_0$-$C_4$alkyl, ($C_3$-$C_7$cycloalkenyl)$C_0$-$C_4$alkyl, (phenyl)$C_0$-$C_2$alkyl, or (heterocycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy, and $R_4$ is hydrogen, $C_1$-$C_6$alkyl, $C_2$-$C_6$alkenyl, or $C_1$-$C_6$alkoxy.

(e) $R_3$ is $C_1$-$C_6$alkyl, ($C_3$-$C_7$cycloalkyl)$C_0$-$C_4$alkyl, or (phenyl)$C_0$-$C_2$alkyl, each of which is substituted with 0 to 3 substituents independently chosen from halogen, hydroxyl, $C_1$-$C_2$alkyl, $C_1$-$C_2$alkoxy, mono- and di-$C_1$-$C_2$alkylamino, $C_1$-$C_2$haloalkyl, and $C_1$-$C_2$haloalkoxy; and $R_4$ is hydrogen, $C_1$-$C_2$alkyl, or $C_1$-$C_2$alkoxy.

(f) $R_3$ is $C_1$-$C_6$alkyl, ($C_3$-$C_7$cycloalkyl)$C_0$-$C_4$alkyl, or (phenyl)$C_0$-$C_2$alkyl.

(g) $R_3$ is $C_1$-$C_6$alkyl.

(h) $R_4$ is hydrogen.

(i) $R_3$ and $R_4$ are be joined to form a cyclopropyl ring, which is substituted with 0 to 2 substituents independently chosen from vinyl, $C_1$-$C_2$alkyl, and $C_1$-$C_2$alkoxy.

(j) $R_{11}$ is $C_1$-$C_6$alkyl, $C_2$-$C_6$alkenyl, $C_2$-$C_6$alkanoyl, or mono- or di-$C_1$-$C_6$alkylamino, ($C_3$-$C_7$cycloalkyl)$C_0$-$C_4$alkyl, ($C_3$-$C_7$cycloalkenyl)$C_0$-$C_4$alkyl, (phenyl)$C_0$-$C_2$alkyl, or (heterocycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy, and $R_{12}$ is hydrogen, $C_1$-$C_6$alkyl, $C_2$-$C_6$alkenyl, or $C_1$-$C_6$alkoxy.

(k) $R_{11}$ is $C_1$-$C_6$alkyl, ($C_3$-$C_7$cycloalkyl)$C_0$-$C_4$alkyl, or (phenyl)$C_0$-$C_2$alkyl, each of which is substituted with 0 to 3 substituents independently chosen from halogen, hydroxyl, $C_1$-$C_2$alkyl, $C_1$-$C_2$alkoxy, mono- and di-$C_1$-$C_2$alkylamino, $C_1$-$C_2$haloalkyl, and $C_1$-$C_2$haloalkoxy; and $R_{12}$ is hydrogen, $C_1$-$C_2$alkyl, or $C_1$-$C_2$alkoxy.

(l) $R_{11}$ is $C_1$-$C_6$alkyl, ($C_3$-$C_7$cycloalkyl)$C_0$-$C_4$alkyl, or (phenyl)$C_0$-$C_2$alkyl.

(m) $R_{11}$ is $C_1$-$C_6$alkyl.

(n) $R_3$ and $R_4$ are be joined to form a cyclopropyl ring, which is substituted with 0 to 2 substituents independently chosen from vinyl, $C_1$-$C_2$alkyl, and $C_1$-$C_2$alkoxy.

(o) The invention includes embodiments in which $R_3$ and $R_{11}$ are joined to form a macrocyclic ring. E.g. the invention includes compounds and salts of Formula II

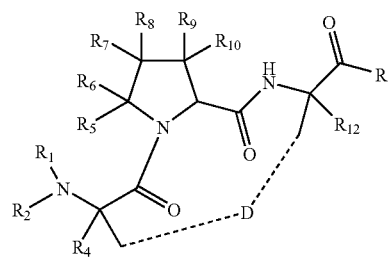

Formula II

Within Formula II D is a alkyl or alkenyl group having 6 to 10 carbon atoms.

(p) For example the invention include compounds and salts of Formula M.

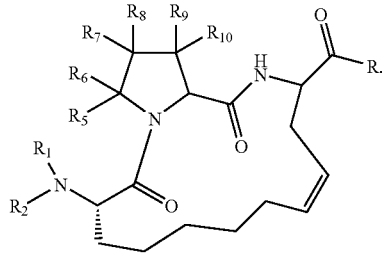

Formula III (q) The invention includes embodiments in which $R_3$ is covalently bound to a cycloalkyl group formed by $R_{11}$ and $R_{12}$ being joined to from a 3- to 7-membered cycloalkyl ring. E.g. the invention includes compounds and salts of Formula IV.

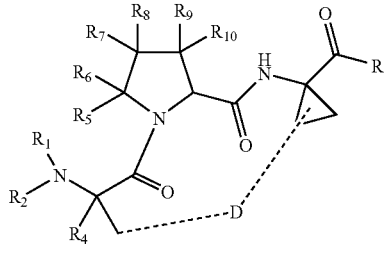

Formula IV

Within Formula IV D is a alkyl or alkenyl group having 6 to 10 carbon atoms.

(r) For example the invention includes compounds and salt of Formula V.

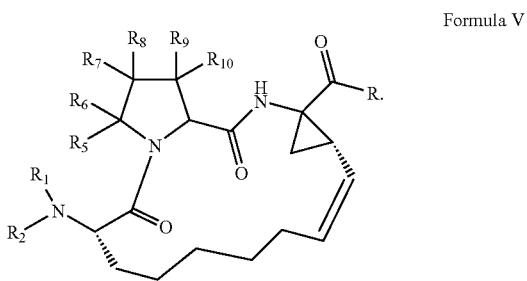

Formula V

The $R_5$, $R_6$, $R_7$, and $R_{10}$ Variables (s) The invention includes compounds and salts of any of the above chemical formulae in which $R_5$, $R_6$, $R_7$, and $R_{10}$ are all hydrogen.

The $R_8$ and $R_9$ Variables (t) $R_8$ is a group of the formula —$(CH_2)_n$Y—Z, where n is 0, 1, or 2, and $R_9$ is hydrogen, halogen, amino, $C_1$-$C_2$alkyl, or $C_1$-$C_2$alkoxy.

(u) n is 0 and Y is —O—, —O(C=O)(NR$_{16}$)—, —NR$_{16}$(C=O)—, or —O(C=O)—.

(v) n is 0 and —O— or —O(C=O)—.

(w) Z is a group of the formula

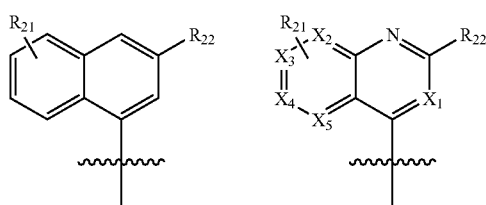

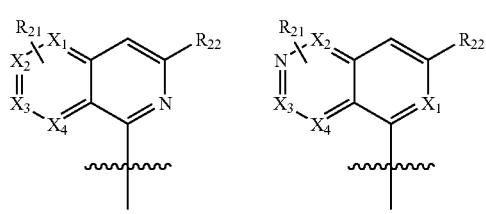

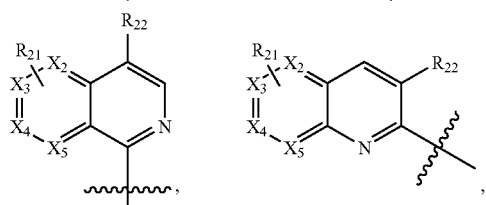

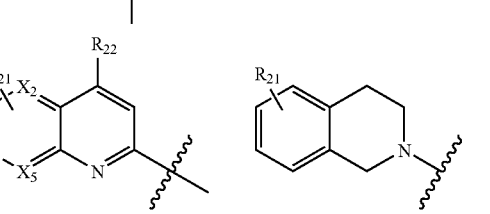

or

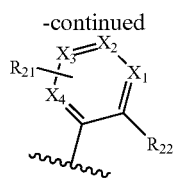

wherein $X_1$, $X_2$, $X_3$, and $X_4$, are independently N or CH and no more than two of $X_1$-$X_4$ are N;

$R_{21}$ represents from 0 to 3 groups independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

$R_{22}$ is hydrogen, halogen, hydroxyl, amino, cyano, —$CONH_2$, —COOH, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy, or $R_{22}$ is ($C_3$-$C_7$cycloalkyl)$C_0C_2$alkyl, (phenyl)$C_0C_2$alkyl, (phenyl)$C_0$-$C_2$alkoxy, (5- or 6-membered heteroaryl)$C_0$-$C_2$alkyl, (5- or 6-membered heteroaryl)$C_0$-$C_2$alkoxy, indanyl, (5- or 6-membered heterocycloalkyl)$C_0C_2$alkyl, or 9- or 10 membered bicyclic heteroaryl, each of which is substituted with 0, 1, or 2 substituents independently chosen from (a) and 0 or 1 substituents (b) where (a) is chosen from halogen, hydroxyl, amino, cyano, nitro, —COOH, —$CONH_2$, $CH_3$(C=O)NH—, $C_1$-$C_4$alkyl, $C_1$-$C_4$alkoxy, $C_1$-$C_4$hydroxyalkyl, mono- and di-$C_1$-$C_4$alkylamino, $C_1$-$C_4$alkylester, mono- and di-$C_1$-$C_4$alkylsulfonamide, mono- and di-$C_1$-$C_4$alkylcarboxamide, $C_1$-$C_2$haloalkyl, and $C_1$-$C_2$haloalkoxy, and (b) is phenyl or 5- or 6-membered heteroaryl, each of which is substituted with 0 or 1 or more of halogen, hydroxyl, $C_1$-$C_4$alkyl, and $C_1$-$C_2$alkoxy.

(x) Z is a group as defined above in (w) and $R_{22}$ is (phenyl)$C_0C_2$alkyl, (phenyl)$C_0$-$C_2$alkoxy, or (5- or 6-membered heteroaryl)$C_0$-$C_2$alkyl, each of which is substituted with 0, 1, or 2 substituents independently chosen from (c) halogen, hydroxyl, amino, cyano, —COOH, —$CONH_2$, $C_1$-$C_2$alkyl, $C_1$-$C_2$alkoxy, mono- and di-$C_1$-$C_2$alkylamino, trifluoromethyl, and trifluoromethoxy.

(y) Z is a group as defined above in (w) and $R_{22}$ is

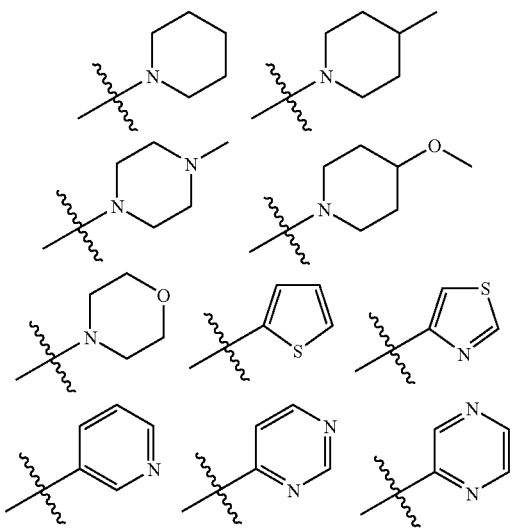

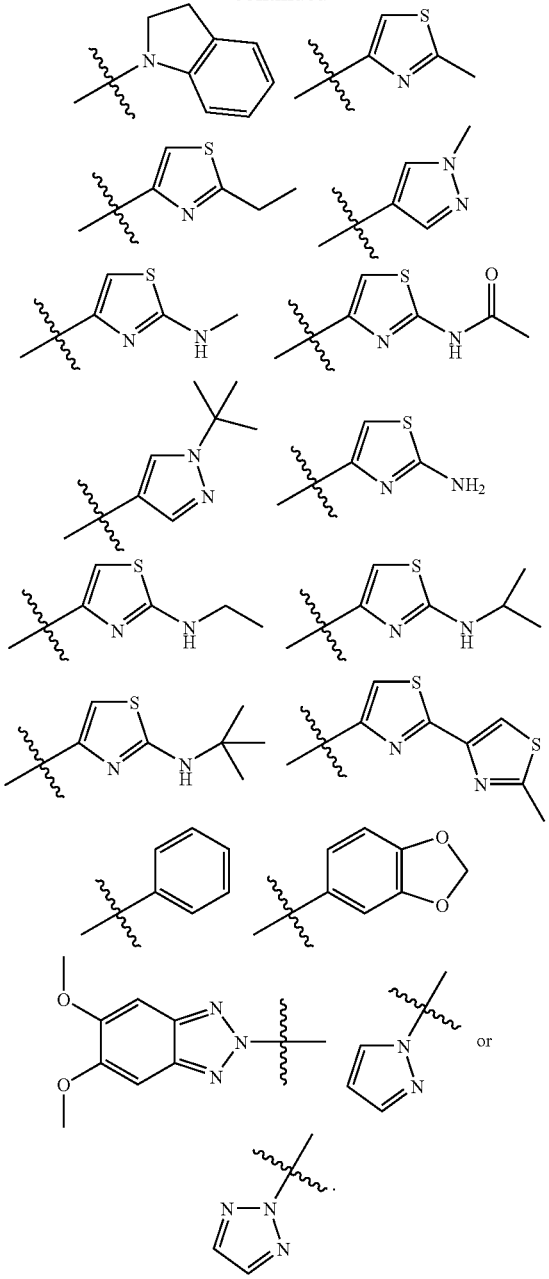

(z) Z is $C_1$-$C_6$alkyl or $C_2$-$C_6$alkenyl, each of which Z is substituted with 0 or 1 or more substituents independently chosen from halogen, hydroxyl, amino, cyano, —$CONH_2$, —COOH, mono- and di-$C_1$-$C_4$alkylsulfonamide, mono- and di-$C_1$-$C_4$alkylcarboxamide, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy.

(aa) Z is (phenyl)$C_0$-$C_2$alkyl, (naphthyl)$C_0$-$C_2$alkyl, (mono- or bicyclic heteroaryl)$C_0$-$C_2$alkyl, or tetrahydroquinolinyl, each of which Z is substituted with 0 or 1 or more substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy, and 0 or 1 $C_3$-$C_7$cycloalkyl, aryl, 5- or 6-membered heteroaryl, indanyl, or 5- or 6-membered heterocycloalkyl, or 9- or 10 membered bicyclic heteroaryl, each of which is substituted with 0, 1, or 2 substituents independently chosen from (a) and 0 or 1 substituents (b) where:

(a) is chosen from halogen, hydroxyl, amino, cyano, nitro, —COOH, —CONH$_2$, =NOH, C$_1$-C$_4$alkyl, C$_1$-C$_4$alkoxy, C$_2$-C$_4$alkanoyl, C$_1$-C$_4$hydroxyalkyl, mono- and di-C$_1$-C$_4$alkylamino, C$_1$-C$_4$alkylester, mono- or di-C$_1$-C$_4$alkylsulfonamide, mono- and di-C$_1$-C$_4$alkylcarboxamide, C$_1$-C$_2$haloalkyl, C$_1$-C$_2$haloalkoxy, and (b) is phenyl and 5- or 6-membered heteroaryl, each of which is substituted with 0 or 1 or more substituents independently chosen from halogen, hydroxyl, amino, —CHO, —COOH, —NH(C—O)H, C$_1$-C$_4$alkyl, C$_1$-C$_2$alkoxy, mono- and di-(C$_1$-C$_4$alkyl)amino, mono- and di-(C$_1$-C$_4$alkyl)carboxamide, C$_1$-C$_4$alkylester, (C$_1$-C$_4$alkylester)amino, C$_1$-C$_2$haloalkyl, and C$_1$-C$_2$haloalkoxy.

(bb) The invention includes compounds and salts of (aa) in which (b) is phenyl, pyridyl, thiazolyl, pyrrolyl, or imidazolyl, each of which is substituted with 0 or 1 or more substituents independently chosen from halogen, hydroxyl, amino, —CHO, —COON, —NH(C=O)H, C$_1$-C$_4$alkyl, C$_1$-C$_2$alkoxy, mono- and di-(C$_1$-C$_4$alkyl)amino, mono- and di-(C$_1$-C$_4$alkyl)carboxamide, C$_1$-C$_4$alkylester, (C$_1$-C$_4$alkylester)amino, C$_1$-C$_2$haloalkyl, and C$_1$-C$_2$haloalkoxy.

(cc) R$_8$ and R$_9$ are taken together to form an optionally substituted 5- to 7-membered cycloalkyl ring.

(dd) R$_8$ and R$_9$ are taken together to form a cyclopentyl ring.

(ee) The invention includes compounds and salts of (cc) in which R$_8$ and R$_9$ are taken together to form a cyclopentyl ring. E.g. the invention includes compounds and salts of Formula VI.

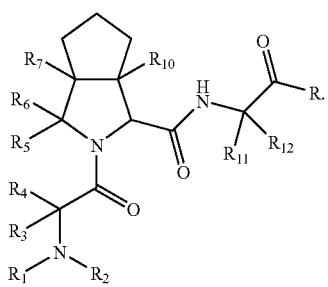

Formula VI (ff) In certain embodiments the invention includes compounds and salts of Formula VI in which R$_3$ is C$_1$-C$_4$alkyl, (C$_3$-C$_7$cycloalkyl)C$_0$-C$_4$alkyl, or (phenyl)C$_0$-C$_2$alkyl, each of which is substituted with 0 to 3 substituents independently chosen from halogen, hydroxyl, C$_1$-C$_2$alkyl, C$_1$-C$_2$alkoxy, mono- and di-C$_1$-C$_2$alkylamino, C$_1$-C$_2$haloalkyl, and C$_1$-C$_2$haloalkoxy; and R$_4$ is hydrogen, C$_1$-C$_2$alkyl, or C$_1$-C$_2$alkoxy; or R$_3$ and R$_4$ are be joined to form a cyclopropyl ring, which is substituted with 0 to 2 substituents independently chosen from vinyl, C$_1$-C$_2$alkyl, and C$_1$-C$_2$alkoxy.

R$_{11}$ is C$_1$-C$_6$alkyl, (C$_3$-C$_7$cycloalkyl)C$_0$-C$_4$alkyl, or (phenyl)C$_0$-C$_2$alkyl, each of which is substituted with 0 to 3 substituents independently chosen from halogen, hydroxyl, C$_1$-C$_2$alkyl, C$_1$-C$_2$alkoxy, mono- and di-C$_1$-C$_2$alkylamino, C$_1$-C$_2$haloalkyl, and C$_1$-C$_2$haloalkoxy; and R$_{12}$ is hydrogen, C$_1$-C$_2$alkyl, or C$_1$-C$_2$alkoxy; or R$_{11}$ and R$_{12}$ are be joined to form a cyclopropyl ring, which is substituted with 0 to 2 substituents independently chosen from vinyl, C$_1$-C$_2$alkyl, and C$_1$-C$_2$alkoxy; and R$_5$, R$_6$, R$_7$, and R$_{10}$ are each independently hydrogen, methyl or methoxy.

(gg) The invention also includes compounds and salts of Formula VII

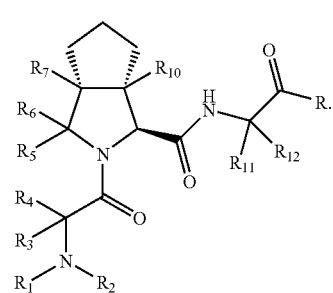

Formula VII (hh) The invention includes compounds and salts of Formula VIII

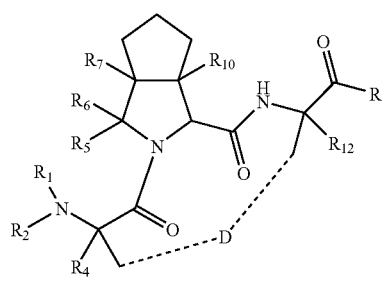

Formula VIII where D is a alkyl or alkenyl group having 6 to 10 carbon atoms;

R$_4$ and R$_{12}$ are independently hydrogen or methyl; and

R$_5$, R$_6$, R$_7$, and R$_{10}$ are independently hydrogen or methyl.

(ii) The invention includes compounds and salts of Formula IX

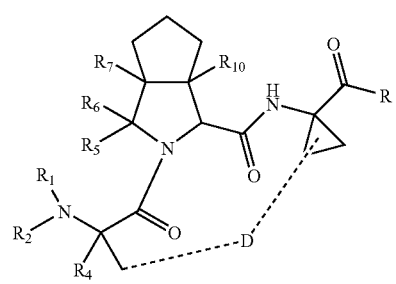

Formula IX where D is a alkyl or alkenyl group having 6 to 10 carbon atoms.

R$_4$ and R$_{12}$ are independently hydrogen or methyl; and

R$_5$, R$_6$, R$_7$, and R$_{10}$ are independently hydrogen or methyl.

The R Variable (jj) R is

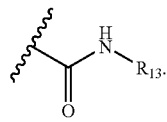

(kk) R is a carboxamide group as shown in (jj) and $R_{13}$ is $C_1$-$C_6$alkyl or $C_2$-$C_6$alkenyl, each of which is substituted with 0 or 1 or more substituents independently chosen from halogen, hydroxyl, amino, cyano, amino, $C_1$-$C_4$alkoxy, mono or di-$C_1$-$C_4$alkylamino.

(ll) R is a carboxamide group as shown in (jj) and $R_{13}$ is ($C_3$-$C_7$cycloalkyl)$C_0$-$C_2$allyl, (aryl)$C_0$-$C_2$alkyl, (5- to 7-membered heterocycloalkyl)$C_0$-$C_2$alkyl, or (heteroaryl)$C_0$-$C_2$alkyl, each of which is substituted with 0 or 1 or more substituents independently chosen from halogen, hydroxyl, amino, cyano, amino, $C_1$-$C_4$alkyl, $C_1$-$C_4$alkoxy, mono or di-$C_1$-$C_4$alkylamino, $C_1$-$C_2$haloalkyl, or $C_1$-$C_2$haloalkoxy.

(mm) R is a carboxamide group as shown in (jj) and $R_{13}$ is $C_3$-$C_7$cycloalkyl which is substituted with 0 or 1 or more substituents independently chosen from halogen, hydroxyl, amino, cyano, amino, $C_1$-$C_2$alkyl, $C_1$-$C_2$alkoxy, mono or di-$C_1$-$C_2$alkylamino.

(nn) R is a carboxamide group as shown in (jj) and $R_{13}$ is $R_{13}$ is cyclopropyl.

Any of the above definitions for the variables R and $R_1$-$R_{12}$ may be combined so long as a stable compound results. All such compounds are included in the scope of the invention.

Pharmaceutical Preparations

Compounds of the invention can be administered as the neat chemical, but are preferably administered as a pharmaceutical composition. Accordingly, the invention provides pharmaceutical formulations comprising a compound or pharmaceutically acceptable salt of the invention, together with at least one pharmaceutically acceptable carrier.

Compounds of the invention may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Binders are substances that bind or "glue" powders together and make them cohesive by forming granules, thus serving as the "adhesive" in the formulation. Binders add cohesive strength to that already available in the diluent or bulking agent. Examples of binders include starch, gelatin, natural sugars, corn sweeteners, natural and synthetic gums such as acacia, sodium alginate, carboxymethylcellulose, polyethylene glycol and waxes. The amount of binder in the composition can range, for example, from about 2 to about 20% by weight of the composition, or from about 3 to about 10% by weight, even more preferably from about 3 to about 6% by weight.

Diluents include sugars such as lactose, sucrose, mannitol and sorbitol; starches derived from wheat, corn, rice and potato; and celluloses such as microcrystalline cellulose. The amount of diluent in the composition may be, for example, about 10 to about 90% by weight of the total composition, about 25 to about 75%, about 30 to about 60% by weight, or about 12 to about 60%.

Disintegrants are materials added to a pharmaceutical composition to help it break apart (disintegrate) and release the active agent. Suitable disintegrants include starches; including "cold water soluble" modified starches such as sodium carboxymethyl starch; natural and synthetic gums such as locust bean, karaya, guar, and tragacanth gum and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range, for example, from about 2 to about 15% by weight of the composition or from about 4 to about 10% by weight.

Lubricants are substances added to a pharmaceutical formulation to enable the tablet, granules, etc. after it has been compressed, to release from the; mold or die by reducing friction or wear. Examples of lubricants useful in pharmaceutical dosage fowls include boric acid, sodium benzoate, sodium acetate, sodium chloride, and the like. Lubricants are usually added at the very last step before tablet compression, since they must be present on the surfaces of the granules and in between them and the parts of the tablet press. The amount of lubricant in the composition can range, for example, from about 0.1 to about 5% by weight of the composition, from about 0.5 to about 2%, or from about 0.3 to about 1.5% by weight. The amount of compound or salt of the invention in a unit dose may be generally varied or adjusted from about 1.0 milligram to about 1,000 milligrams, from about 1.0 to about 900 milligrams, from about 1.0 to about 500 milligrams, or from about 1 to about 250 milligrams, according to the particular application and the potency of the compound. The actual dosage employed may be varied depending upon the patient's age, sex, weight and severity of the condition being treated.

Pharmaceutical compositions formulated for oral administration are often preferred. These compositions contain between 0.1 and 99% of a compound of the invention and usually at least about 5% (weight %) of a compound of the invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, tinctures, syrups, or elixirs, for example. Moreover, formulations containing these compounds can be presented as a dry product, e.g. as granules or powders, for constitution with water or other suitable vehicle before use. Typical components of carriers for syrups, elixirs, emulsions and suspensions include ethanol, glycerol, propylene glycol, polyethylene glycol, liquid sucrose, sorbitol and water. Liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid). Oral formulations may contain demulcent, flavoring agents, sweetening agents, such as sucrose or saccharin, taste-masking agents, and coloring agents.

Suspensions

Aqueous suspensions contain the active material(s) in admixture with excipients suitable for the manufacture of aqueous suspensions. Such excipients are suspending agents, for example AVICEL RC-591, sodium carboxymethylcellulose, methylcellulose, hydropropylmethylcellulose, sodium alginate, polyvinylpyrrolidone, gum tragacanth and gum acacia; dispersing or wetting agents, for example lecithin and polysorbate 80. The aqueous suspensions may also contain one or more preservatives, for example ethyl, n-propyl p-hydroxybenzoate, methyl parabens, propyl parabens, and sodium benzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard or soft shell capsules. A capsule is a dosage form administered in a special container or enclosure containing an active agent. The active agent may be present in solid, liquid, gel, or powder form, or any other pharmaceutically acceptable form. A capsule shell may be made of methyl cellulose, polyvinyl alcohols, or denatured gelatins or starch or other material. Hard shell capsules are typically made of blends of relatively high gel strength bone and pork skin gelatins. Soft shell capsule shells are often made of animal or plant gelatins. The capsule itself may contain small amounts of dyes, opaquing agents, plasticizers and preservatives.

The active agent in a capsule may be mixed with an inert solid diluent, for example, calcium carbonate, calcium phosphate or kaolin, or in the case of soft gelatin capsules the active ingredient may be mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier typically comprises least about 90% by weight of the total composition.

Methods of Treatment

The invention includes methods of preventing and treating hepatitis C infections, by providing an effective amount of a compound of the invention to patient at risk for hepatitis C infection or infected with a hepatitis C virus.

The pharmaceutical combinations disclosed herein are useful for preventing and treating hepatitis C infections in patients. An effective amount of a pharmaceutical combination of the invention may be an amount sufficient to (a) prevent hepatitis C or a symptom of a hepatitis C from occurring in a patient who may be predisposed to hepatitis C but has not yet been diagnosed as having it or prevent diseases that may be associated with or caused by a primary hepatitis C infection (such as liver fibrosis that can result in the context of chronic HCV infection); (b) inhibit the progression of hepatitis C; and (c) cause a regression of the hepatitis C infection. An amount of a pharmaceutical composition effect to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

The invention also includes using pharmaceutical combinations comprising a compound of the invention and at least one additional active agent in prophylactic therapies. In the context of prophylactic or preventative treatment an effective amount of a compound of the invention is an amount sufficient to significantly decrease the patient's risk of contracting a hepatitis C infection.

Methods of treatment include providing certain dosage amounts of a compound of the invention and the at least one additional active agent to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration. Dosage emit forms will generally contain between from about 1 mg to about 500 mg of each active agent. In certain embodiments 25 mg to 500 mg, or 25 mg to 200 mg of a compound of the invention are provided daily to a patient. When the additional active agent is NM 283 (valopicitabine), 100 mg to 1000 mg/day, or 200 mg to 800 mg/day, or 200 to 400 mg/day of either of those agents are typically provided to the patient. When the additional active agent is VX-950, 1000 mg to 3750 mg/day, or 1200 mg to 1800 mg/day are administered to the patient. Treatment regiments in which VX-950 is an additional active agent and about 350 to about 450 mg or about 700 to about 800 mg of VX-950 are administered to a patient three times per day or about 350 to about 450 mg or about 700 to about 800 mg is administered every 12 hours are particularly included in the invention.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Combination Methods

The invention includes methods of treatment in which a compound or salt of the invention is provided together with one or more additional active agents. In certain embodiments the active agent (or agents) is an HCV protease inhibitor or HCV polymerase inhibitor. For example the protease inhibitor may be telaprevir (VX-950) and the polymerase inhibitor may be valopicitabine, or NM 107, the active agent which valopicitabine is converted into in vivo.

According to the methods of the invention, the compound of the invention and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound of The invention and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments method of treatment includes providing a patient with a compound of Formula I and an interferon such as a pegylated interferon or interferon gamma. The interferon may be the only compound provided with the compound of the invention or may be provided with an additional active agent that is not an interferon.

The invention methods of treatment and pharmaceutical combinations including compounds of the invention any one or combination of the following compounds and substances as an additional active agent:

Caspase inhibitors: IDN 6556 (Idun Pharmaceuticals)

Cyclophilin Inhibitors: NIM811 (Novartis) and DEBIO-025 (Debiopharm)

Cytochrome P450 monooxygenase inhibitors: ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole Glucocorticoids: hydrocortisone, cortisone, prednisone, prednisolone, methylprednisolone, triamcinolone, paramethasone, betamethasone, and dexamethasone Hematopoietins: hematopoietin-1 and hematopoietin-2. Other members of the hematopoietin superfamily such as the various colony stimulating factors (e.g. (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietin, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha nl from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), unpegylated interferon alpha, alpha interferon, and its analogs, and synthetic thymosin alpha 1 (ZADAXIN, SciClone Pharmaceuticals Inc.)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (XTL), HuMax-HepC (Genmab), Hepatitis C Immune Globin (human) (CIVACIR, Nabi Biopharmaceuticals)

Nucleoside analogues: Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), and viramidine (Valeant Pharmaceuticals), an amidine prodrug of ribavirin. Combinations of nucleoside analogues may also be employed.

Non-nucleoside inhibitors: PSI-6130 (Roche/Pharmasset), delaviridine (RESCRIPTOR, Pfizer), and HCV-796 (Viropharm)

P7 protein inhibitor: amantadine (SYMMETREL, Endo Pharmaceuticals, Inc.)

Polymerase inhibitors: NM283 (valopicitabine) (Idenix) and NM 107 (Idenix).

Protease inhibitors: BILN-2061 (Boehringer Ingelheim), GW-433908 (prodrug of Amprenavir, Glaxo/Vertex), indinavir (CRIXIVAN, Merck), ITMN-191 (Intermune/Array Biopharma), VX950 (Vertex) and combinations comprising one or more of the foregoing protease inhibitors RNA interference: SIRNA-034 RNAi (Sirna Therapeutics)

Therapeutic Vaccines: IC41 (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), TLR7 agonist (Anadys Pharmaceuticals), CPG10101 (Coley), and TLR9 agonists including CPG 7909 (Coley)

Cyclophilin Inhibitors: NIM811 (Novartis) and DEBIO-025 (Debiopharm)

Patients receiving hepatitis C medications are typically given interferon together with another active agent. Thus methods of treatment and pharmaceutical combinations in which a compound of The invention is provided together with an interferon, such as pegylated interferon alfa 2a, as the additional active agents are included as embodiments. Similarly methods and pharmaceutical combinations in which ribavirin is an additional active agent are provided herein.

EXAMPLES

All nonaqueous reactions are performed under an atmosphere of dry argon gas (99.99%). NMR spectra are recorded at ambient temperature using a Bruker Avance 300 spectrometer (1H at 300.1 MHz and $^{13}$C at 75.5 MHz,). The chemical shifts for $^1$H and $^{13}$C are reported in parts per million ($\delta$) relative to external tetramethylsilane and are referenced to signals of residual protons in the deuterated solvent. Analytical HPLC is performed using a Waters X-bridge C18 150×4.6 mm 3.5 μm column with a 20-min linear gradient elution of increasing concentrations of acetonitrile in water (5 to 95%) containing 0.1% trifluoroacetic acid with a flow rate of 1.0 mL/min and UV detection at 254 nm. Low-resolution mass spectra are recorded on a Thermo Finnigan Surveyor MSQ instrument (operating in APCI mode) equipped with a Gilson liquid chromatograph. Unless noted otherwise, the quasi-molecular ions, [M+H]$^+$, observed in the low-resolution mass spectra are the base peaks.

This invention is further illustrated by the following examples that should not be construed as limiting.

Abbreviations

The following chemical abbreviations are used in Examples 1 to 3. Additional abbreviations used in these examples will be familiar to those of skill in the art of organic chemical synthesis.

| | |
|---|---|
| AcOEt | Ethyl Acetate |
| AIBN | 2,2'-azobis(2-methylpropionitrile) |
| BOC | t-Butoxycarbonyl |
| $(BOC)_2O$ | di-t-Butyl dicarbonate |
| c. | concentrated |
| CDI | 1,1'-Carbonyldiimidazole |
| DCM | dichloromethane |
| DIPEA | Diisopropylethylamine |
| EDCI | 1-Ethyl-3-[3-dimethylaminopropyl]carbodiimide |
| $Et_3N$ | triethylamine |
| EtOH | Ethanol |
| Hex. | Hexanes |
| MeOH | Methanol |
| TFA | Trifluoroacetic acid |
| THF | tetrahydrofuran |
| TLC | Thin Layer Chromatography |

Example 1

Synthesis of Tertiary Amine Substituted Thiazoles (Compounds 20-25)

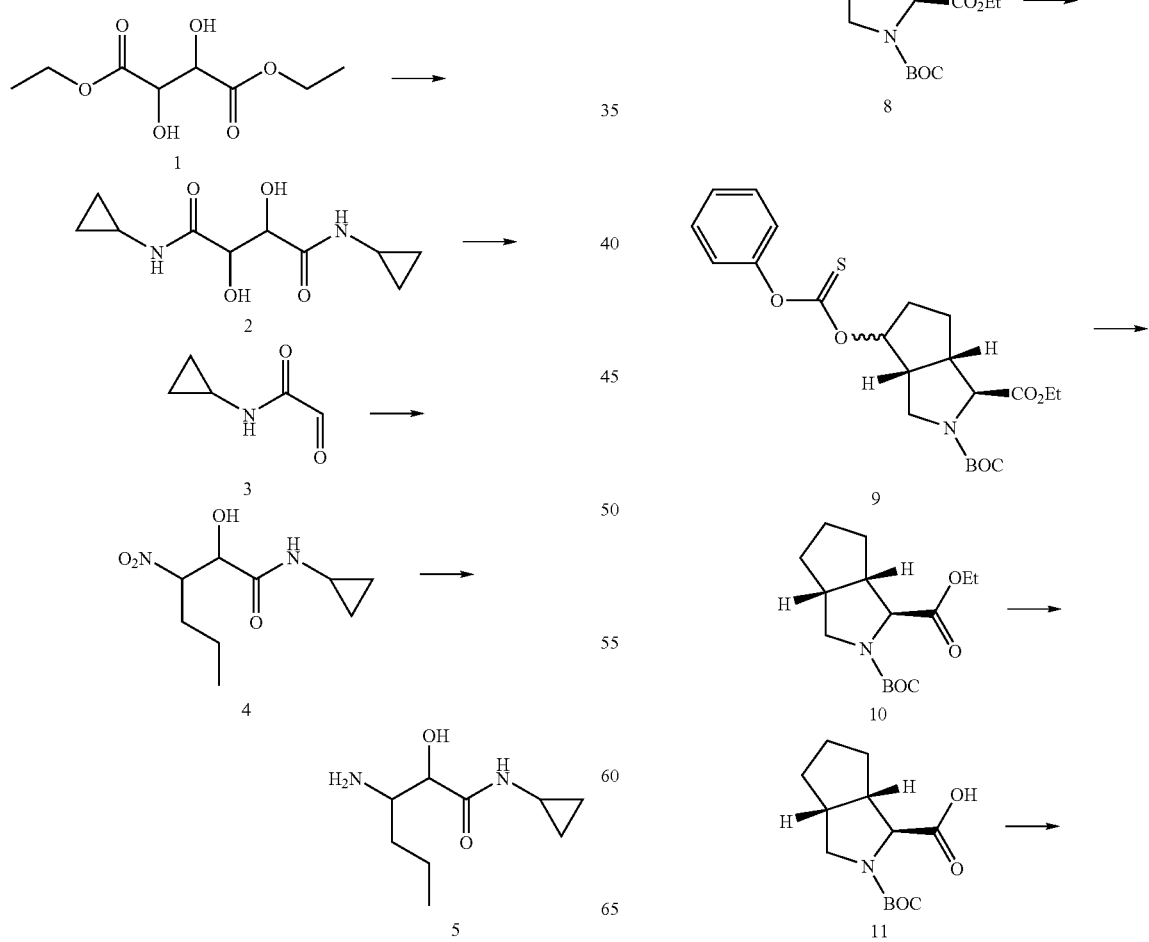

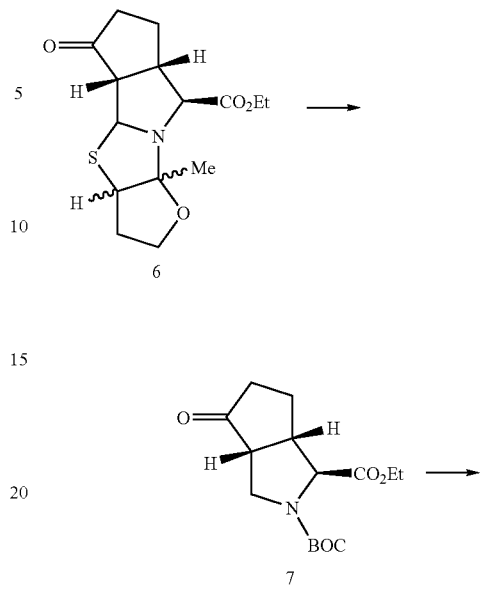

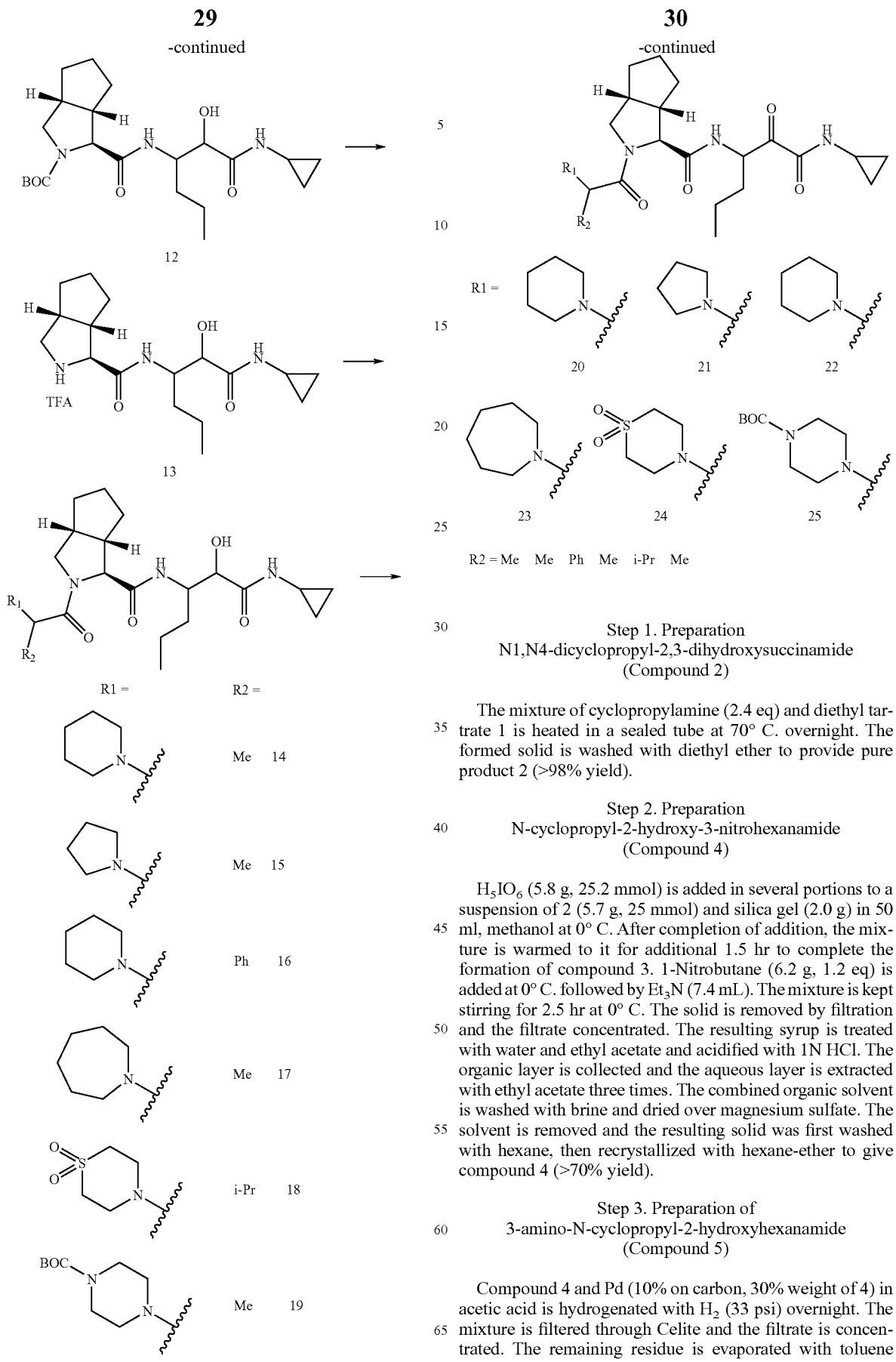

Step 1. Preparation N1,N4-dicyclopropyl-2,3-dihydroxysuccinamide (Compound 2)

The mixture of cyclopropylamine (2.4 eq) and diethyl tartrate 1 is heated in a sealed tube at 70° C. overnight. The formed solid is washed with diethyl ether to provide pure product 2 (>98% yield).

Step 2. Preparation N-cyclopropyl-2-hydroxy-3-nitrohexanamide (Compound 4)

$H_5IO_6$ (5.8 g, 25.2 mmol) is added in several portions to a suspension of 2 (5.7 g, 25 mmol) and silica gel (2.0 g) in 50 ml, methanol at 0° C. After completion of addition, the mixture is warmed to it for additional 1.5 hr to complete the formation of compound 3. 1-Nitrobutane (6.2 g, 1.2 eq) is added at 0° C. followed by $Et_3N$ (7.4 mL). The mixture is kept stirring for 2.5 hr at 0° C. The solid is removed by filtration and the filtrate concentrated. The resulting syrup is treated with water and ethyl acetate and acidified with 1N HCl. The organic layer is collected and the aqueous layer is extracted with ethyl acetate three times. The combined organic solvent is washed with brine and dried over magnesium sulfate. The solvent is removed and the resulting solid was first washed with hexane, then recrystallized with hexane-ether to give compound 4 (>70% yield).

Step 3. Preparation of 3-amino-N-cyclopropyl-2-hydroxyhexanamide (Compound 5)

Compound 4 and Pd (10% on carbon, 30% weight of 4) in acetic acid is hydrogenated with $H_2$ (33 psi) overnight. The mixture is filtered through Celite and the filtrate is concentrated. The remaining residue is evaporated with toluene twice and then diethyl ether is added to give compound 5.

Step 4. Preparation or (1S,3aR,6aS)-ethyl-2-BOC substituted-4-oxooctahydrocyclopenta[c]pyrrole-1-carboxylate (Compound 7)

Bu$_3$SnH (Aldrich, 36 ml, 136 mmol) followed by AIBN (2.5 g, 15 mmol) is added into the tetra cyclic compound 6 (31.1 g, 100 mmol; prepared with Monn's method reported in JOC 59, 2773, 1994) dissolved in anhydrous toluene (160 ml). The mix is degassed and refluxed under Ar till starting material disappears 6 hr) as shown by TLC (Hex/AcOEt, 1/1). Toluene is evaporated under reduced pressure and the oil residue is treated with diethyl ether (100 ml) and HCl aq. solution (1.0 N, 110 ml). After vigorous stirring for over night, diethyl ether is separated. The aqueous layer was extracted with diethyl ether (100 ml×6) and then used for next step.

(BOC)$_2$O (32.7 g, 150 mmol) dissolved in THF is added into the aqueous solution obtained above, (100 ml) followed by NaOH aq (4.5 g in water 10 ml). The mixture is then cooled in an ice bath. The mix is stirred for 1 hr and NaCl (s, 30 g) is then added and stirred. The organic layer and the aqueous layer are extracted with AcOEt (50 ml×3). The combined organic layer is washed with brine and dried over anhydrous sodium sulfate. After evaporation, the oily crude is applied to silica gel chromatography with Hex/AcOEt (4:1 to 3:1) as eluant. Compound 7 (25 g, 84%) is obtained as colorless liquid.

Step 5. Preparation of (1S,3aR,6aS)-ethyl 2-BOC-4-hydroxyoctahydrocyclopenta[c]pyrrole-1-carboxylate (Compound 8)

NaBH$_4$ (2.6 g, 67.3 mmol) is added in three portions at 0° C. with stirring to a solution of compound 7 (20 g, 67.3 mmol) in EtOH (150 ml). The mix is stirred for additional 1 hr for completion before AcOH (10 ml) is carefully added at 0° C. to quench the reaction. EtOH is removed by evaporation and the residue is dissolved in AcOEt (300 ml) to perform the aqueous work up. After washing with sat NaHCO$_3$ (100 ml×2) and brine (100 ml) and drying over NaSO$_4$, the AcOEt solution is passed through a short bed of silica gel. The solvent is evaporated to give compound 8 (19.2 g, 95%) as colorless syrup.

Step 6. Preparation of (1S,3aR,6aS)-ethyl 2-BOC-4-(phenoxycarbonothioyloxy)octahydrocyclopenta[c]pyrrole-1-carboxylate (Compound 9)

O-Phenyl chlorothionoformate (10 ml, 70.6 mmol) is added with stirring at 0° C. under Ar atmosphere, into the solution of compound 8 (19.2 g, 64.2 mmol) in DCM (150 ml), followed by pyridine (6.22 ml, 77.04 mmol). The mix is stirred at rt over night. Methanol (5 ml) is added to destroy excessive phenyl chlorothionocabonate before performing an aqueous work up. The organic layer is washed with 1N HCl (100 ml), water (100 ml), sat NaHCO$_3$ (100 ml), and brine (100 ml) in sequence. After drying over NaSO$_4$, the solvent is removed by evaporation to give compound 9 (27.5 g, 99%) as golden color syrup.

Step 7. Preparation of (1S,3aR,6aS)-ethyl 2-BOC-octahydrocyclopenta[c]pyrrole-1-carboxylate (Compound 10)

Bu$_3$SnH (25 ml, 94.8 mmol) followed by AIBN (1.55 g, 9.48 mmol) is added at room temperature into the solution of compound 9 (27.5 g, 63.2 mmol) in benzene (60 ml). The mix is degassed twice and stirred at reflux temperature under Ar for 4 hr. Volatiles are evaporated and the residue is applied to flash chromatography on silica gel with Hex/AcOEt (gradient 9/1 to 6/1) as eluant. Compound 10 (13 g, 73%) is obtained as colorless liquid.

Step 8. Preparation of (1S,3aR,6aS)-2-BOC-octahydrocyclopenta[c]pyrrole-1-carboxylic acid (Compound 11)

Compound 10 (13 g, 46 mmol) is treated with 2N NaOH (44 ml) in EtOH (120 ml) at rt for 3 hr. Volatiles are evaporated and the residue is dissolved in water (50 ml). 1N HCl is added to adjust pH to and the aqueous solution is back extracted with DCM (100 ml×3). The DCM is evaporated to give compound 11 (8.5 g, 72%) as colorless syrup.

Step 9. Preparation (1S,3aR,6aS)-N-(1-(cyclopropylamino)-2-hydroxy-1-oxohexan-3-yl)-2-BOC-octahydrocyclopenta[c]pyrrole-1-carboxamide (Compound 12)

Compound 11 (3.06 g, 12 mmol) is treated with EDCI (2.3 g, 12 mmol) and HOBt (1.84 g, 12 mmol) in DCM (50 ml) for 10 min. Compound 5 (1.79 g, 9.6 mmol) followed by DIPEA (2.6 ml, 15 mmol) is added and the mix is stirred at rt over night. The mixture is evaporated to remove solvent and the residue is treated with AcOEt (200 ml). After washing with 1N HCl 20 ml, sat. NaHCO$_3$ 50 ml×3, and brine (50 ml) in sequence and then drying over NaSO$_4$, solvent is removed by evaporation to give compound 12 (3.85 g, 95%) as a white foam.

Step 10. Preparation of (1S,3aR,6aS)—N-(1-(cyclopropylamino)-2-hydroxy-1-oxohexan-3-yl)octahydrocyclopenta[c]pyrrole-1-carboxamide (Compound 13)

Compound 12 (0.845 g, 2 mmol) is treated with TFA (5 ml) in DCM (10 ml) at 0° C. for 2 hr. The mixture is evaporated to dryness. The yellow syrup so obtained is dissolved in DCM (20 ml) to make a stock solution of 13 (0.1 M) for the next step.

Step 11. Preparation of (1S,3aR,6aS)—N-(1-(cyclopropylamino)-2-hydroxy-1-oxohexan-3-yl)-2-(2-(piperidin-1-yl)propanoyl)octahydrocyclopenta[c]pyrrole-1-carboxamide and related compounds (Compound 14-19)

2-Piperidin-1-yl-propionic acid hydrochloride (63 mg, 0.4 mmol) is treated with EDCI (77 mg, 0.4 mmol) and HOBt (61 mg, 0.4 mmol) in DCM (2 ml) for 10 min. Stock solution of compound 13 (0.1 M, 4 ml) followed by DIPEA (0.122 ml, 0.7 mmol) is added and the mix is stirred at rt over night. Aqueous work up with AcOEt extraction and sat. NaHCO$_3$ wash gives compound 14 (crude, 68 mg) after removal of solvent. Starting from corresponding acids, compounds 15-19 were prepared with similar method.

Step 12. Preparation of (1S,3aR,6aS)—N-(1-(cyclopropylamino)-1,2-dioxohexan-3-yl)-2-(2-(piperidin-1-yl)propanoyl)octahydrocyclopenta[c]pyrrole-1-carboxamide and related compounds (Compound 20-25)

Compound 14 (68 mg) is treated with Dess-Martin reagent (100 mg) in DCM (5 ml) at rt for 2 hr. The mix is concentrated and then applied to HPLC for purification. Compound 20 (17 mg) is obtained as its TFA salt. Compounds 21-25 are obtained via similar methods.
Example 2
Synthesis of (3R,5S)-5-(1-(cyclopropylamino)-1,2-dioxohexan-3-ylcarbamoyl)-1-(2-(piperidin-1-yl)propanoyl)pyrrolidin-3-yl 3,4-dihydroisoquinoline-2(1H)-carboxylate (Compound 33)
The syntheses of compounds 33 and 34 is depicted in Scheme 2.
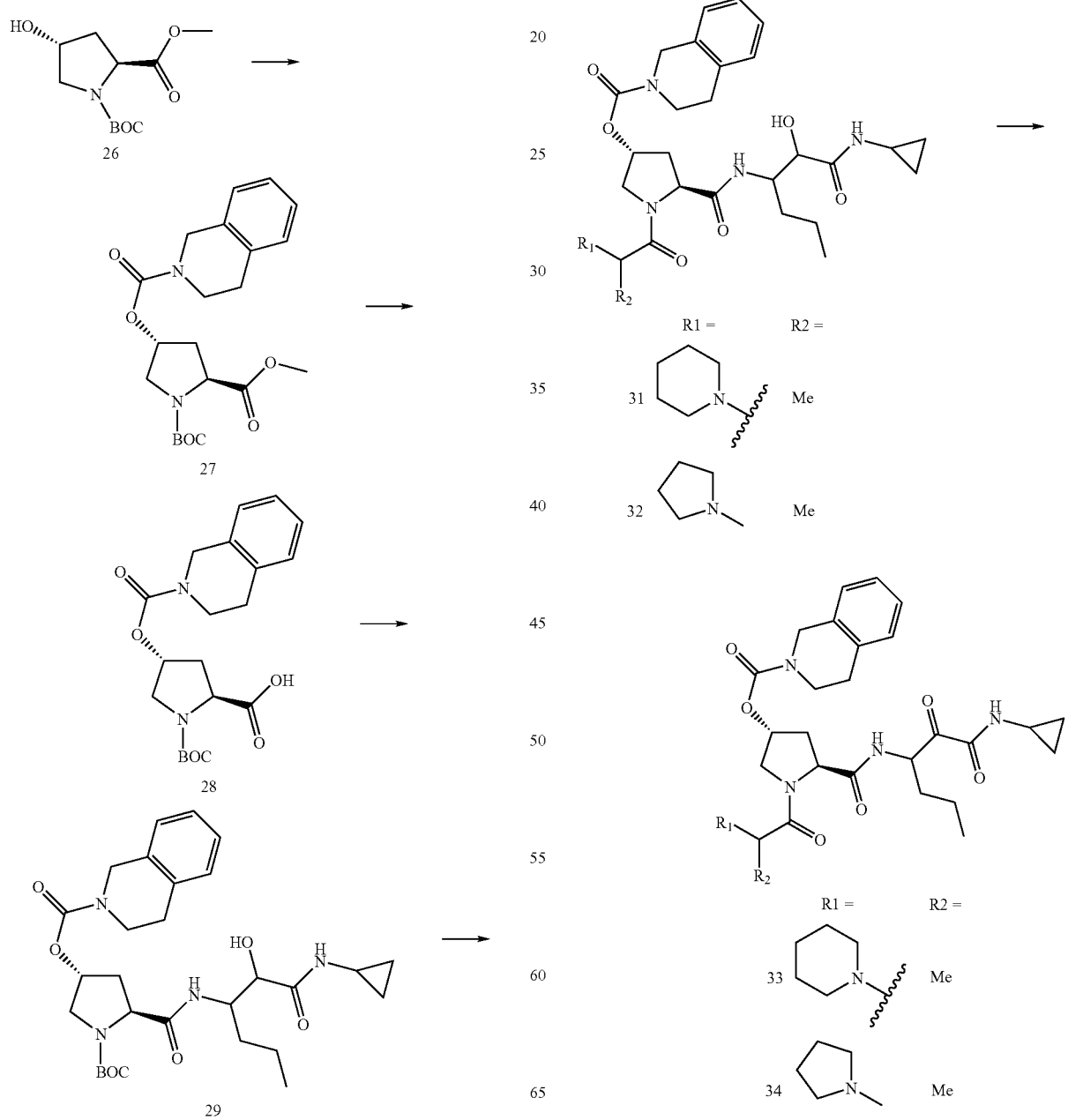

Step 1. Preparation of (3R,5S)-5-(methoxycarbonyl)-1-BOC-pyrrolidin-3-yl 3,4-dihydroisoquinoline-2(1H)-carboxylate (Compound 27)

Add Boc-trans-L-4-hydroxyproline methyl ester 26 (2.45 g, 10 mmol) dissolved in DCM (15 ml) dropwise into CDI (1.62 g, 10 mmol) solution in DCM (80 ml) at 0° C. After stirring at rt for 2 hr, 1,2,3,4-tetrahydroisoquinoline (0.543 g, 4.08 mmol) in DCM (5 ml) is added and the mixture is stirred over night. The solvent is removed and residue applied to aqueous workup. The ethyl acetate (200 ml) layer is washed with 1N HCl (20 ml×2), sat. sodium bicarbonate aqueous (30 ml×3), brine (10 ml) sequentially and dried over anhydrous sodium sulfate. Filter and remove the solvent by evaporation to provide compound 27 (3.89 g, 96%) as yellow syrup.

Step 2. Preparation of (2S,4R)-1-BOC-4-(1,2,3,4-tetrahydroisoquinoline-2-carbonyloxy)pyrrolidine-2-carboxylic acid (Compound 28)

Compound 27 (3.89 g, 9.6 mmol) in MeOH (35 ml) is treated with 2N NaOH (15 ml) at rt for 3 hr. Solvent is removed by evaporation and the residue dissolved in water (50 ml). Add c. HCl to adjust pH to ~2. The precipitate is collected by filtration and dried to give compound 28 (3.34 g, 89%) as a white powder.

Step 3. Preparation of (3R,5S)-5-(1-(cyclopropylamino)-2-hydroxy-1-oxohexan-3-ylcarbamoyl)-1-BOC-pyrrolidin-3-yl-3,4-dihydroisoquinoline-2(1H)-carboxylate (Compound 29)

Compound 28 (2.67 g, 6.85 mmol) is treated with EDCI (1.33 g, 6.85 mmol) and HOBt (1.06 g, 6.85 mmol) in DCM (50 ml) for 10 min. Compound 5 (1.15 g, 6.2 mmol) followed by DIPEA (2.2 ml, 12.4 mmol) is added and the mix is stirred at rt over night. The mixture is evaporated to remove solvent and the residue treated with AcOEt (100 ml). After washing with 1N HCl 20 ml, sat. NaHCO$_3$ 30 ml×3, and brine 50 ml in sequence and then drying over NaSO$_4$, solvent is removed by evaporation to give compound 29 (2.6 g, 75%) as white foam.

Step 4. Preparation of (3R,5S)-5-(1-(cyclopropylamino)-2-hydroxy-1-oxohexan-3-ylcarbamoyl)pyrrolidin-3-yl-3,4-dihydroisoquinoline-2(1H)-carboxylate (Compound 30)

Compound 29 (2.6 g, 4.65 mmol) in DCM (25 ml) is treated with TFA (25 ml) at 0° C. for 1 hr. Volatiles are evaporated to dryness. The residue is dissolved in AcOEt (100 ml) and washed with sat. NaHCO$_3$ (10 ml×3) and brine (2 ml). After drying over NaSO$_4$, the solvent is removed by evaporation to give compound 30 (1.75 g, 82%) as pale yellow powder.

Step 5. Preparation of (3R,5S)-5-(1-(cyclopropylamino)-2-hydroxy-1-oxohexan-3-ylcarbamoyl)-1-(2-(piperidin-1-yl)propanoyl)pyrrolidin-3-yl-3,4-dihydroisoquinoline-2(1H)-carboxylate and related compound (Compound 31 and 32)

2-Piperidin-1-yl-propionic acid hydrochloride (58 mg, 0.3 mmol) is treated with EDCI (63 mg, 0.3 mmol) and HOBt (46 mg, 0.3 mmol) in DCM (5 ml) for 10 min. Compound 30 (0.138 g, 0.3 mmol) followed by DIPEA (0.104 ml, 0.6 mmol) is added and the mix is stirred at rt over night. Aqueous work up with AcOEt extraction and sat NaHCO$_3$ wash provides compound 31 (crude, 182 mg) after removal of solvent.

Starting form corresponding acid, compound 32 (crude, 170 mg) is prepared with similar method.

Step 6. Preparation of (3R,5S)-5-(1-(cyclopropylamino)-1,2-dioxohexan-3-ylcarbamoyl)-1-(2-(piperidin-1-yl)propanoyl)pyrrolidin-3-yl-3,4-dihydroisoquinoline-2(1H)-carboxylate (Compound 33 and 34)

Compound 31 (182 mg) is treated with Dess-Martin reagent (170 mg) in DCM (5 ml) at rt for 2 hr. The mix is concentrated and then applied to HPLC for purification. Compound 33 (47 mg) is obtained as pale yellow foam. Compounds 34 (36 mg) is obtained via a similar method.

Example 3

Synthesis of Macrocyclic Peptide Ketoamides

The synthesis of macro cyclic peptide keto amide is performed as depicted in Scheme 3.

Scheme 3.

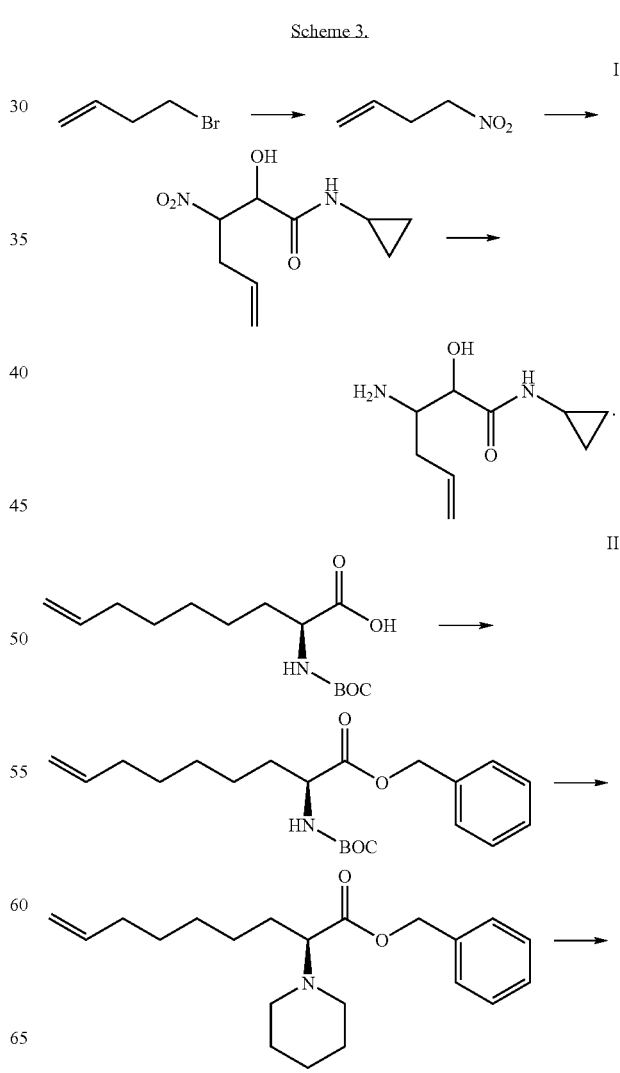

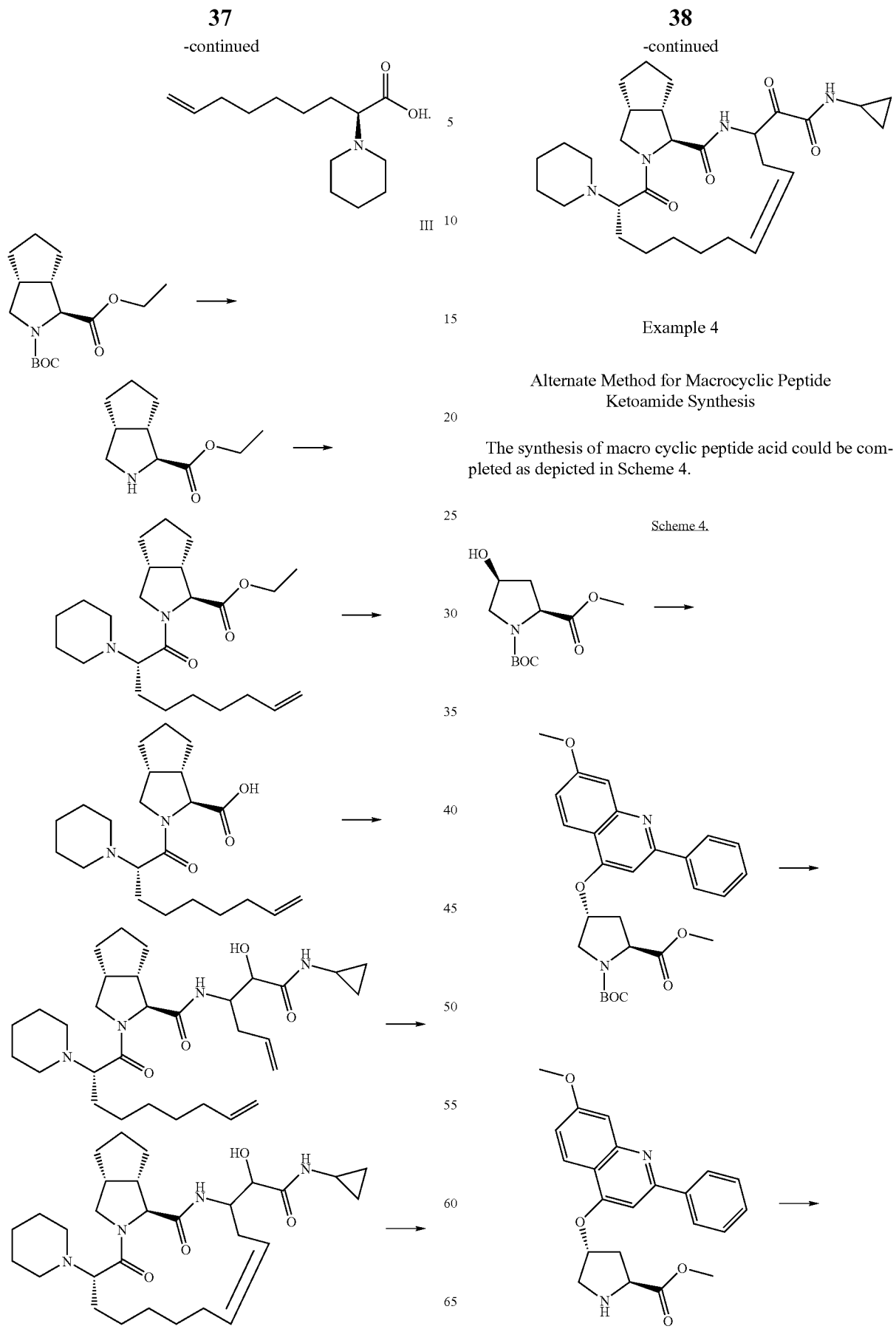
Example 4
Alternate Method for Macrocyclic Peptide Ketoamide Synthesis
The synthesis of macro cyclic peptide acid could be completed as depicted in Scheme 4.
Scheme 4.

39

-continued

40

-continued

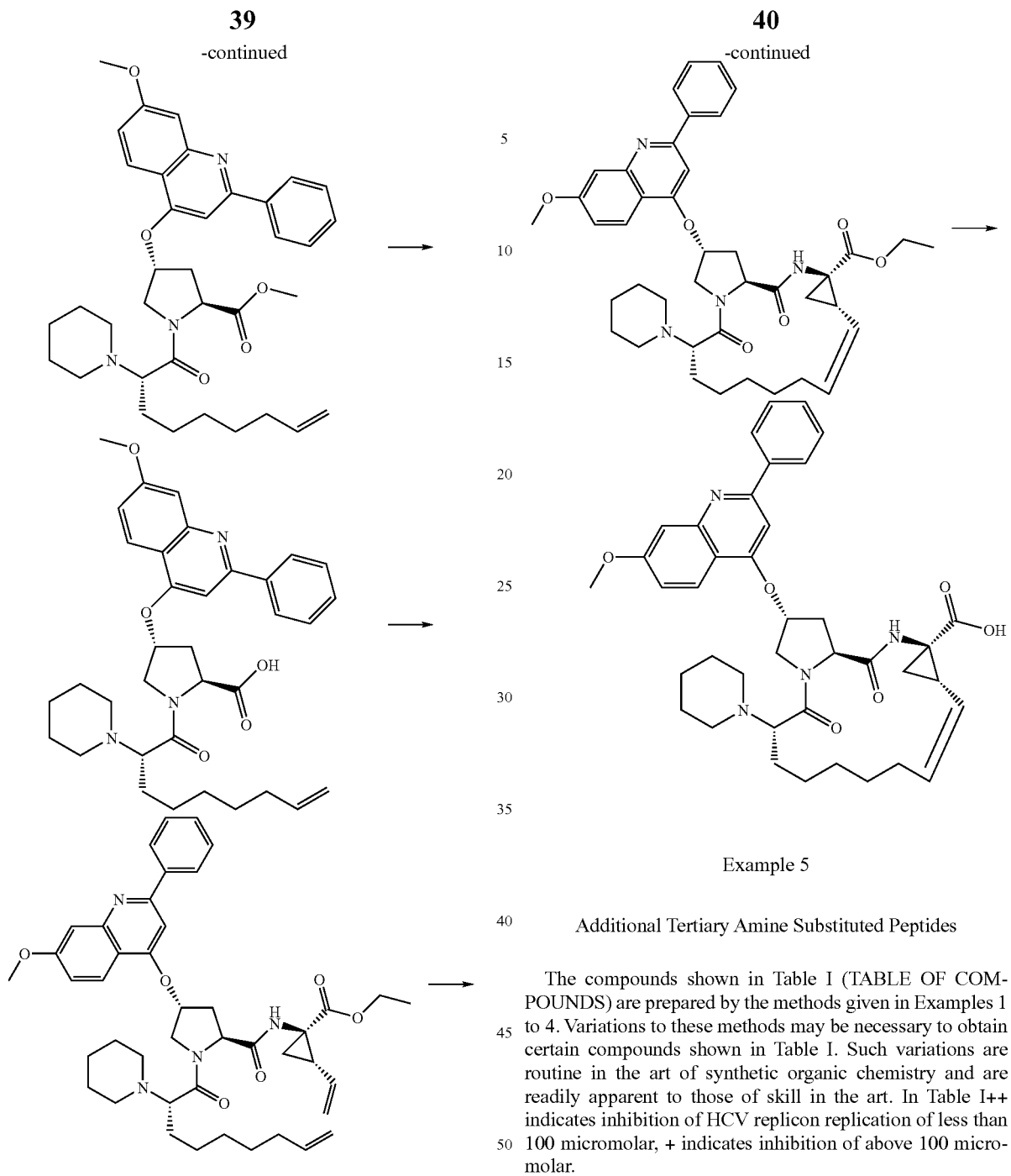

Example 5

Additional Tertiary Amine Substituted Peptides

The compounds shown in Table I (TABLE OF COMPOUNDS) are prepared by the methods given in Examples 1 to 4. Variations to these methods may be necessary to obtain certain compounds shown in Table I. Such variations are routine in the art of synthetic organic chemistry and are readily apparent to those of skill in the art. In Table I++ indicates inhibition of HCV replicon replication of less than 100 micromolar, + indicates inhibition of above 100 micromolar.

| Cmp. # | Structure | Name | EC50 |
|---|---|---|---|
| 35 | 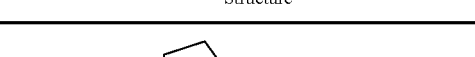 | N-(1-(cyclopropylamino)-1,2-dioxohexan-3-yl)-2-(2-(piperidin-1-yl)propanoyl)octahydrocyclopenta[c]pyrrole-1-carboxamide | ++ |

-continued

| Cmp. # | Structure | Name | EC50 |
|---|---|---|---|
| 36 | 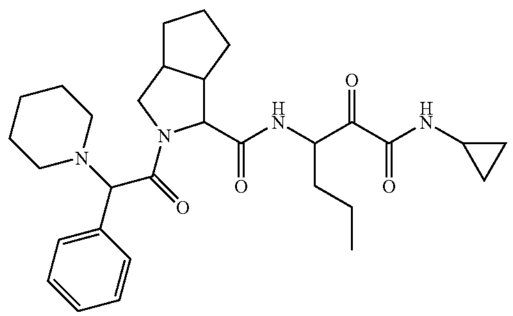 [SMILES: CCCC(NC(=O)C1C2CCCC2CN1C(=O)C(c1ccccc1)N1CCCCC1)C(=O)C(=O)NC1CC1] | N-(1-(cyclopropylamino)-1,2-dioxohexan-3-yl)-2-(2-phenyl-2-(piperidin-1-yl)acetyl)octahydrocyclopenta[c]pyrrole-1-carboxamide | ++ |
| 37 | 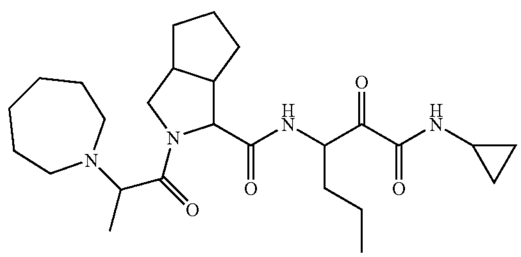 [SMILES: CCCC(NC(=O)C1C2CCCC2CN1C(=O)C(C)N1CCCCCC1)C(=O)C(=O)NC1CC1] | 2-(2-(azepan-1-yl)propanoyl)-N-(1-(cyclopropylamino)-1,2-dioxohexan-3-yl)octahydrocyclopenta[c]pyrrole-1-carboxamide | ++ |
| 39 | 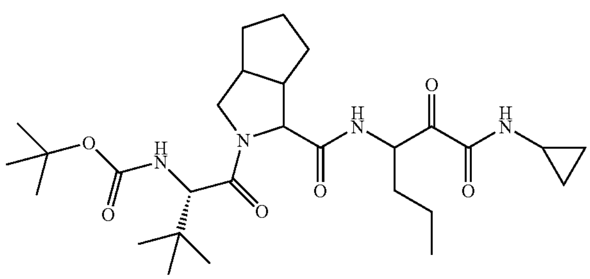 [SMILES: CCCC(NC(=O)C1C2CCCC2CN1C(=O)[C@@H](NC(=O)OC(C)(C)C)C(C)(C)C)C(=O)C(=O)NC1CC1] | tert-butyl(2S)-1-(1-(1-(cyclopropylamino)-1,2-dioxohexan-3-ylcarbamoyl)hexahydrocyclopenta[c]pyrrol-2(1H)-yl)-3,3-dimethyl-1-oxobutan-2-ylcarbamate | ++ |
| 40 | 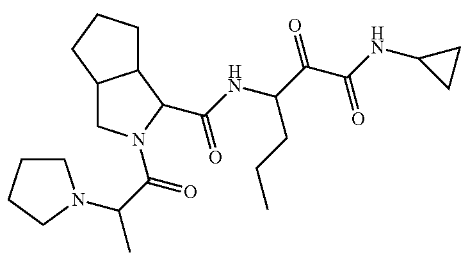 [SMILES: CCCC(NC(=O)C1C2CCCC2CN1C(=O)C(C)N1CCCC1)C(=O)C(=O)NC1CC1] | N-(1-(cyclopropylamino)-1,2-dioxohexan-3-yl)-2-(2-(pyrrolidin-1-yl)propanoyl)octahydrocyclopenta[c]pyrrole-1-carboxamide | ++ |
| 41 | 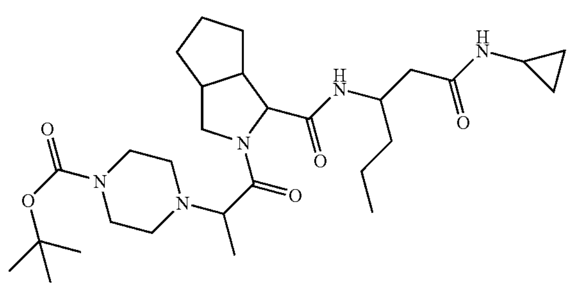 [SMILES: CCCC(CC(=O)NC1CC1)NC(=O)C1C2CCCC2CN1C(=O)C(C)N1CCN(C(=O)OC(C)(C)C)CC1] | tert-butyl 4-(1-(1-(1-(cyclopropylamino)-1,2-dioxohexan-3-ylcarbamoyl)hexahydrocyclopenta[c]pyrrol-2(1H)-yl)-1-oxopropan-2-yl)piperazine-1-carboxylate | ++ |

| Cmp. # | Structure | Name | EC50 |
| --- | --- | --- | --- |
| 42 | 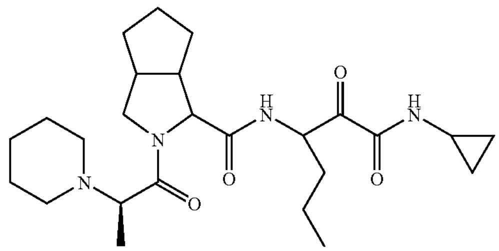 [SMILES: CCCC(NC(=O)C1C2CCCC2CN1C(=O)[C@@H](C)N1CCCCC1)C(=O)C(=O)NC1CC1] | N-(1-(cyclopropylamino)-1,2-dioxohexan-3-yl)-2-((R)-2-(piperidin-1-yl)propanoyl)octahydrocyclopenta[c]pyrrole-1-carboxamide | + |
| 43 | 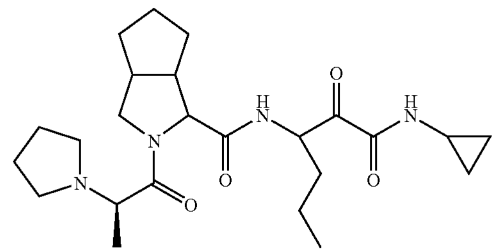 [SMILES: CCCC(NC(=O)C1C2CCCC2CN1C(=O)[C@@H](C)N1CCCC1)C(=O)C(=O)NC1CC1] | N-(1-(cyclopropylamino)-1,2-dioxohexan-3-yl)-2-((R)-2-(pyrrolidin-1-yl)propanoyl)octahydrocyclopenta[c]pyrrole-1-carboxamide | + |
| 44 | 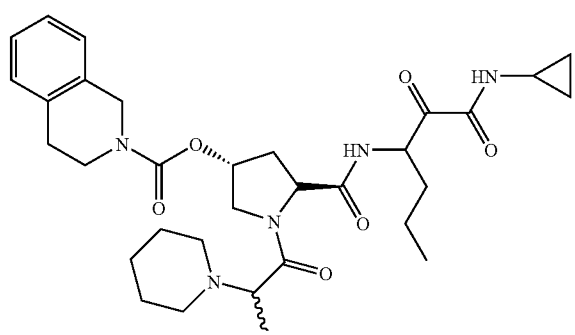 | (3R,5S)-5-(1-(cyclopropylamino)-1,2-dioxohexan-3-ylcarbamoyl)-1-(2-(piperidin-1-yl)propanoyl)pyrrolidin-3-yl 3,4-dihydroisoquinoline-2(1H)-carboxylate | ++ |
| 45 | 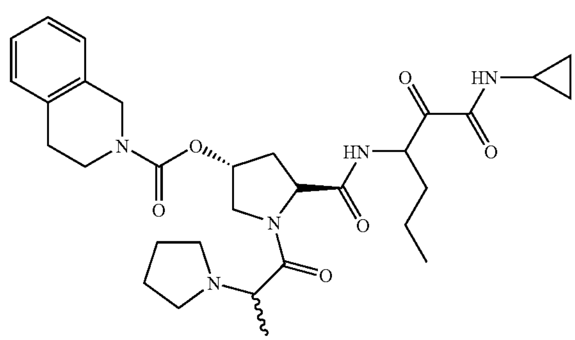 | (3R,5S)-S-(1-(cyclopropylamino)-1,2-dioxohexan-3-ylcarbamoyl)-1-(2-(pyrrolidin-1-yl)propanoyl)pyrrolidin-3-yl 3,4-dihydroisoquinoline-2(1H)-carboxylate | + |
| 46 | 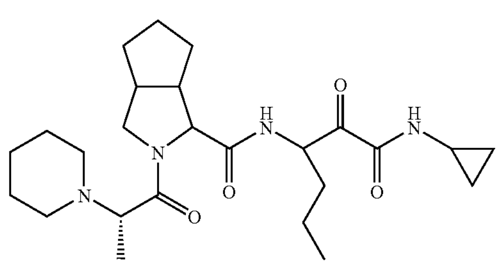 [SMILES: CCCC(NC(=O)C1C2CCCC2CN1C(=O)[C@H](C)N1CCCCC1)C(=O)C(=O)NC1CC1] | N-(1-(cyclopropylamino)-1,2-dioxohexan-3-yl)-2-((S)-2-(piperidin-1-yl)propanoyl)octahydrocyclopenta[c]pyrrole-1-carboxamide | ++ |

-continued

| Cmp. # | Structure | Name | EC50 |
|---|---|---|---|
| 47 | 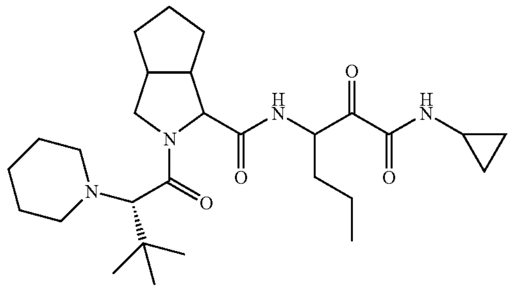 [SMILES: CCCC(NC(=O)C1C2CCCC2CN1C(=O)[C@@H](N1CCCCC1)C(C)(C)C)C(=O)C(=O)NC1CC1] | N-(1-(cyclopropylamino)-1,2-dioxohexan-3-yl)-2-((S)-3,3-dimethyl-2-(piperidin-1-yl)butanoyl)octahydrocyclopenta[c]pyrrole-1-carboxamide | ++ |
| 48 | 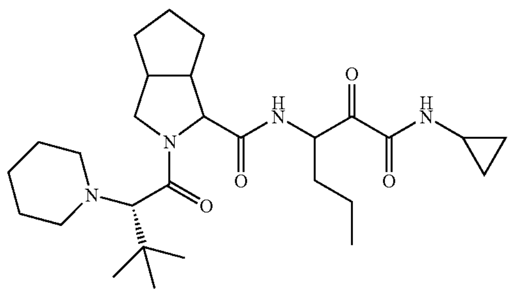 [SMILES: CCCC(NC(=O)C1C2CCCC2CN1C(=O)[C@@H](N1CCCCC1)C(C)(C)C)C(=O)C(=O)NC1CC1] | N-(1-(cyclopropylamino)-1,2-dioxohexan-3-yl)-2-((S)-3,3-dimethyl-2-(piperidin-1-yl)butanoyl)octahydrocyclopenta[c]pyrrole-1-carboxamide | ++ |
| 49 | 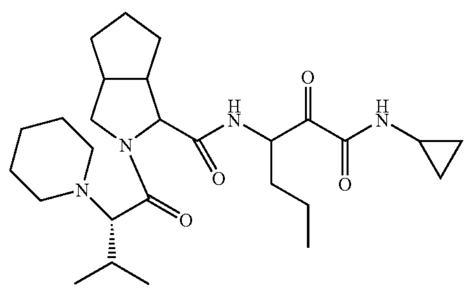 [SMILES: CCCC(NC(=O)C1C2CCCC2CN1C(=O)[C@H](C(C)C)N1CCCCC1)C(=O)C(=O)NC1CC1] | N-(1-(cyclopropylamino)-1,2-dioxohexan-3-yl)-2-((S)-3-methyl-2-(piperidin-1-yl)butanoyl)octahydrocyclopenta[c]pyrrole-1-carboxamide | ++ |
| 50 | 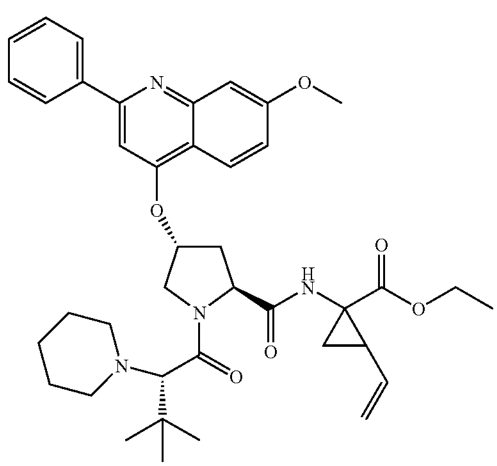 [SMILES: C=CC1CC1(NC(=O)[C@@H]1C[C@@H](Oc2cc(-c3ccccc3)nc3cc(OC)ccc23)CN1C(=O)[C@@H](N1CCCCC1)C(C)(C)C)C(=O)OCC] | ethyl 1-((2S,4R)-1-((S)-3,3-dimethyl-2-(piperidin-1-yl)butanoyl)-4-(7-methoxy-2-phenylquinolin-4-yloxy)pyrrolidine-2-carboxamido)-2-vinylcyclopropanecarboxylate | ++ |

| Cmp. # | Structure | Name | EC50 |
|---|---|---|---|
| 51 | 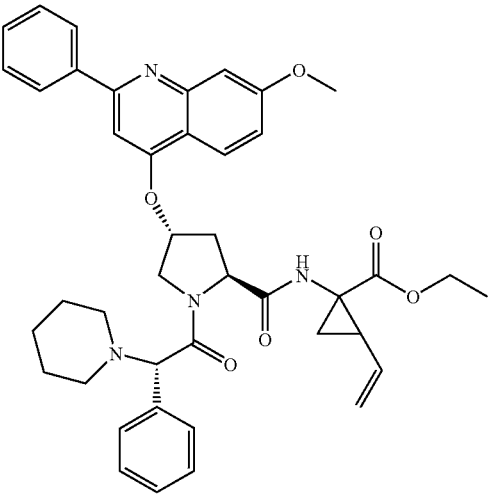 [SMILES: C=CC1CC1(NC(=O)[C@@H]1C[C@@H](Oc2cc(-c3ccccc3)nc3cc(OC)ccc23)CN1C(=O)[C@H](c1ccccc1)N1CCCCC1)C(=O)OCC] | ethyl 1-((2S,4R)-4-(7-methoxy-2-phenylquinolin-4-yloxy)-1-((S)-2-phenyl-2-(piperidin-1-yl)acetyl)pyrrolidine-2-carboxamido)-2-vinylcyclopropanecarboxylate | ++ |
| 52 | 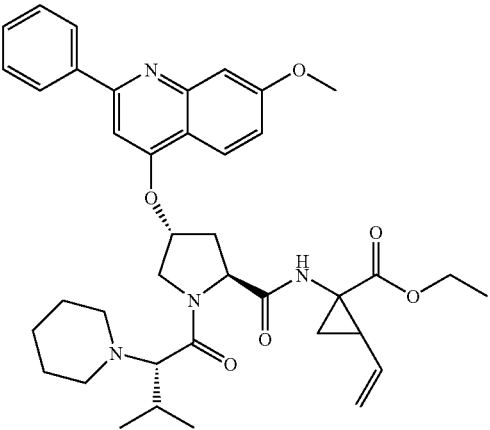 [SMILES: C=CC1CC1(NC(=O)[C@@H]1C[C@@H](Oc2cc(-c3ccccc3)nc3cc(OC)ccc23)CN1C(=O)[C@H](C(C)C)N1CCCCC1)C(=O)OCC] | ethyl 1-((2S,4R)-4-(7-methoxy-2-phenylquinolin-4-yloxy)-1-((S)-3-methyl-2-(piperidin-1-yl)butanoyl)pyrrolidine-2-carboxamido)-2-vinylcyclopropanecarboxylate | ++ |
| 53 | 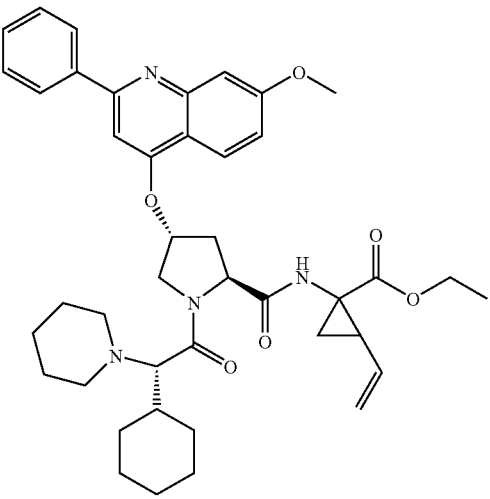 [SMILES: C=CC1CC1(NC(=O)[C@@H]1C[C@@H](Oc2cc(-c3ccccc3)nc3cc(OC)ccc23)CN1C(=O)[C@H](C1CCCCC1)N1CCCCC1)C(=O)OCC] | ethyl 1-((2S,4R)-1-((S)-2-cyclohexyl-2-(piperidin-1-yl)acetyl)-4-(7-methoxy-2-phenylquinolin-4-yloxy)pyrrolidine-2-carboxamido)-2-vinylcyclopropanecarboxylate | ++ |

| Cmp. # | Structure | Name | EC50 |
|---|---|---|---|
| 54 | 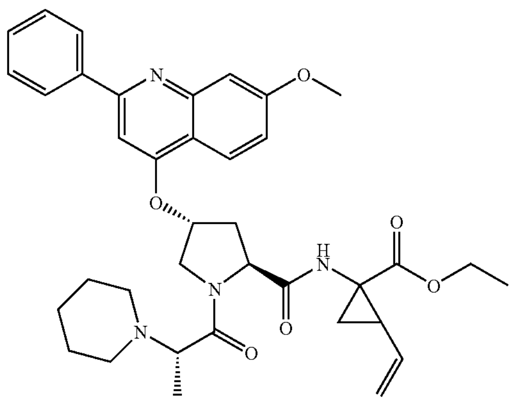 [SMILES: C=CC1CC1(NC(=O)[C@@H]1C[C@@H](Oc2cc(-c3ccccc3)nc3cc(OC)ccc23)CN1C(=O)[C@H](C)N1CCCCC1)C(=O)OCC] | ethyl 1-((2S,4R)-4-(7-methoxy-2-phenylquinolin-4-yloxy)-1-((S)-2-(piperidin-1-yl)propanoyl)pyrrolidine-2-carboxamido)-2-vinylcyclopropanecarboxylate | ++ |
| 55 | 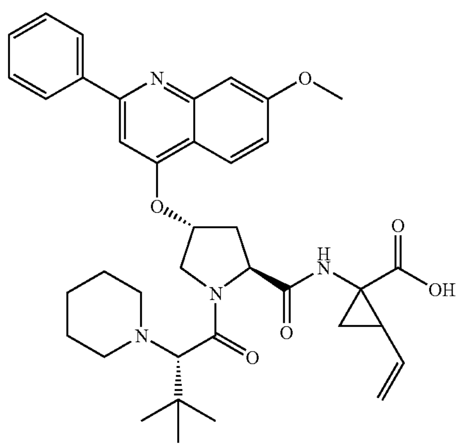 [SMILES: C=CC1CC1(NC(=O)[C@@H]1C[C@@H](Oc2cc(-c3ccccc3)nc3cc(OC)ccc23)CN1C(=O)[C@@H](N1CCCCC1)C(C)(C)C)C(=O)O] | 1-((2S,4R)-1-((S)-3,3-dimethyl-2-(piperidin-1-yl)butanoyl)-4-(7-methoxy-2-phenylquinolin-4-yloxy)pyrrolidine-2-carboxamido)-2-vinylcyclopropanecarboxylic acid | ++ |
| 56 | 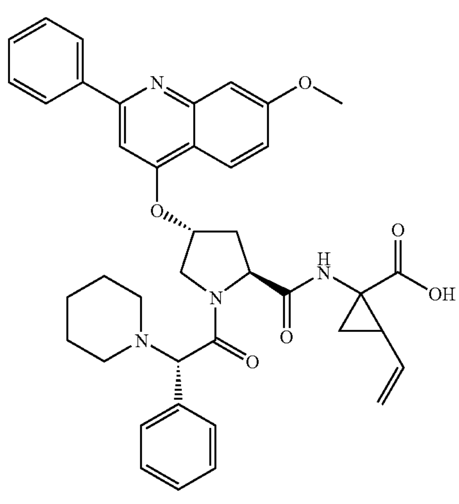 [SMILES: C=CC1CC1(NC(=O)[C@@H]1C[C@@H](Oc2cc(-c3ccccc3)nc3cc(OC)ccc23)CN1C(=O)[C@H](c1ccccc1)N1CCCCC1)C(=O)O] | 1-((2S,4R)-4-(7-methoxy-2-phenylquinolin-4-yloxy)-1-((S)-2-phenyl-2-(piperidin-1-yl)acetyl)pyrrolidine-2-carboxamido)-2-vinylcyclopropanecarboxylic acid | + |

| Cmp. # | Structure | Name | EC50 |
|---|---|---|---|
| 57 | 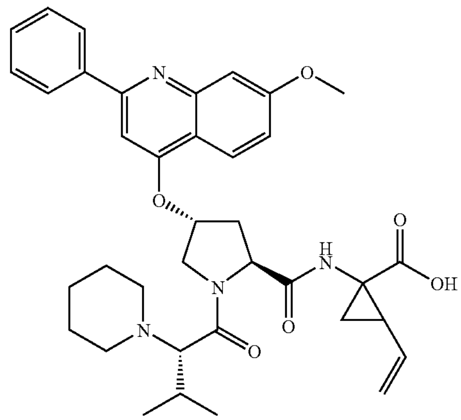 [SMILES: C=CC1CC1(NC(=O)[C@@H]1C[C@@H](Oc2cc(-c3ccccc3)nc3cc(OC)ccc23)CN1C(=O)[C@H](C(C)C)N1CCCCC1)C(=O)O] | 1-((2S,4R)-4-(7-methoxy-2-phenylquinolin-4-yloxy)-1-((S)-3-methyl-2-(piperidin-1-yl)butanoyl)pyrrolidine-2-carboxamido)-2-vinylcyclopropanecarboxylic acid | ++ |
| 58 | 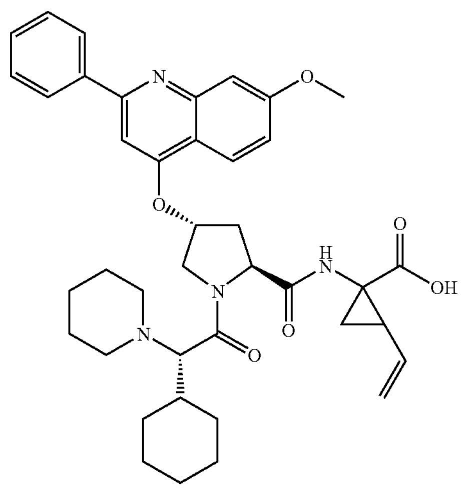 [SMILES: C=CC1CC1(NC(=O)[C@@H]1C[C@@H](Oc2cc(-c3ccccc3)nc3cc(OC)ccc23)CN1C(=O)[C@H](C1CCCCC1)N1CCCCC1)C(=O)O] | 1-((2S,4R)-1-((S)-2-cyclohexyl-2-(piperidin-1-yl)acetyl)-4-(7-methoxy-2-phenylquinolin-4-yloxy)pyrrolidine-2-carboxamido)-2-vinylcyclopropanecarboxylic acid | ++ |
| 59 | 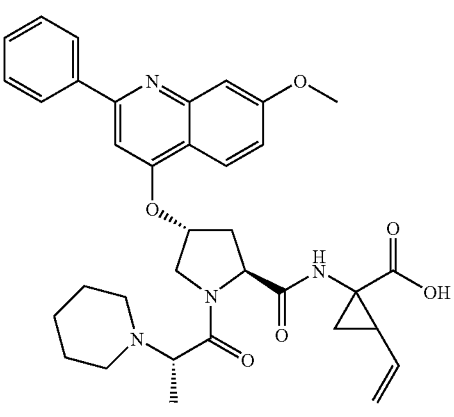 [SMILES: C=CC1CC1(NC(=O)[C@@H]1C[C@@H](Oc2cc(-c3ccccc3)nc3cc(OC)ccc23)CN1C(=O)[C@H](C)N1CCCCC1)C(=O)O] | 1-((2S,4R)-4-(7-methoxy-2-phenylquinolin-4-yloxy)-1-((S)-2-(piperidin-1-yl)propanoyl)pyrrolidine-2-carboxamido)-2-vinylcyclopropanecarboxylic acid | + |

-continued

| Cmp. # | Structure | Name | EC50 |
|---|---|---|---|
| 60 | 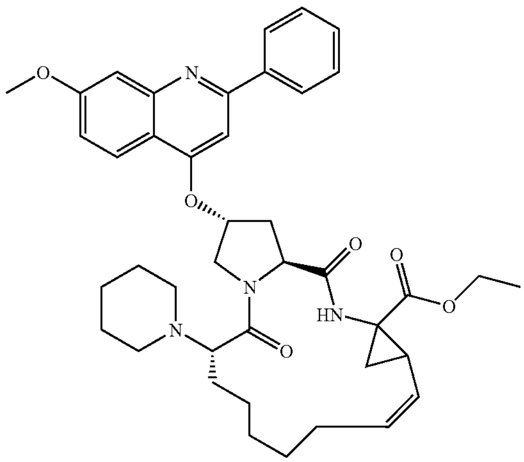 [SMILES: CCOC(=O)C12CC1/C=C\CCCCC[C@H](N1CCCCC1)C(=O)N1C[C@H](Oc3cc(-c4ccccc4)nc4cc(OC)ccc34)C[C@H]1C(=O)N2] | (2R,6S,16aS,Z)-ethyl 2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate | ++ |
| 61 | 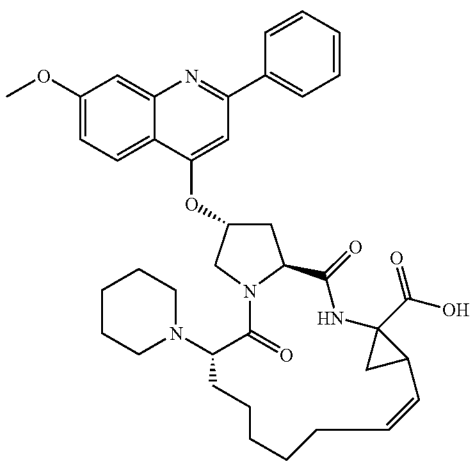 [SMILES: COc1ccc2c(O[C@@H]3C[C@H]4C(=O)NC5(C(=O)O)CC5/C=C\CCCCC[C@H](N5CCCCC5)C(=O)N4C3)cc(-c3ccccc3)nc2c1] | (2R,6S,16aS,Z)-2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid | ++ |
| 62 | 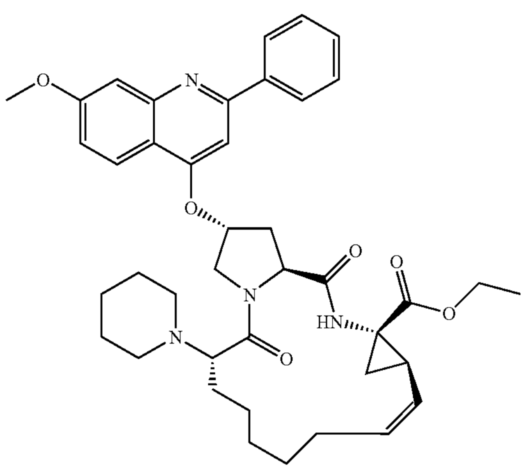 [SMILES: CCOC(=O)[C@]12C[C@@H]1/C=C\CCCCC[C@H](N1CCCCC1)C(=O)N1C[C@H](Oc3cc(-c4ccccc4)nc4cc(OC)ccc34)C[C@H]1C(=O)N2] | (2R,6S,13aR,14aS,16aS,Z)-ethyl 2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate | ++ |

| Cmp. # | Structure | Name | EC50 |
|---|---|---|---|
| 63 | 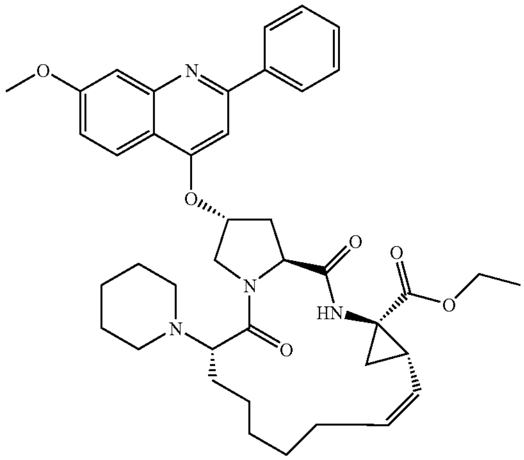 [SMILES: CCOC(=O)[C@@]12C[C@H]1/C=C\CCCCC[C@H](N1CCCCC1)C(=O)N1C[C@H](Oc3cc(-c4ccccc4)nc4cc(OC)ccc34)C[C@H]1C(=O)N2] | (2R,6S,13aS,14aR,16aS,Z)-ethyl 2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate | ++ |
| 64 | 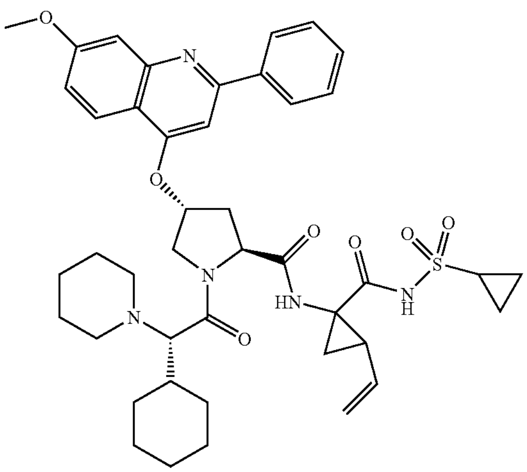 [SMILES: C=CC1CC1(NC(=O)[C@@H]1C[C@@H](Oc2cc(-c3ccccc3)nc3cc(OC)ccc23)CN1C(=O)[C@H](C1CCCCC1)N1CCCCC1)C(=O)NS(=O)(=O)C1CC1] | (2S,4R)-1-((S)-2-cyclohexyl-2-(piperidin-1-yl)acetyl)-N-(1-(cyclopropylsulfonylcarbamoyl)-2-vinylcyclopropyl)-4-(7-methoxy-2-phenylquinolin-4-yloxy)pyrrolidine-2-carboxamide | ++ |
| 65 | 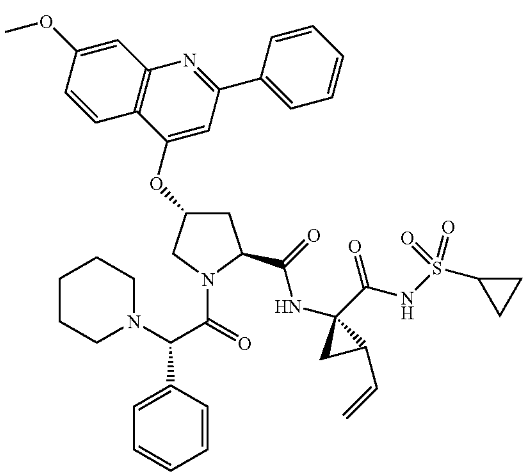 | (2S,4R)-N-((1S,2R)-1-(cyclopropylsulfonylcarbamoyl)-2-vinylcyclopropyl)-4-(7-methoxy-2-phenylquinolin-4-yloxy)-1-((S)-2-phenyl-2-(piperidin-1-yl)acetyl)pyrrolidine-2-carboxamide | ++ |

| Cmp. # | Structure | Name | EC50 |
|---|---|---|---|
| 66 | 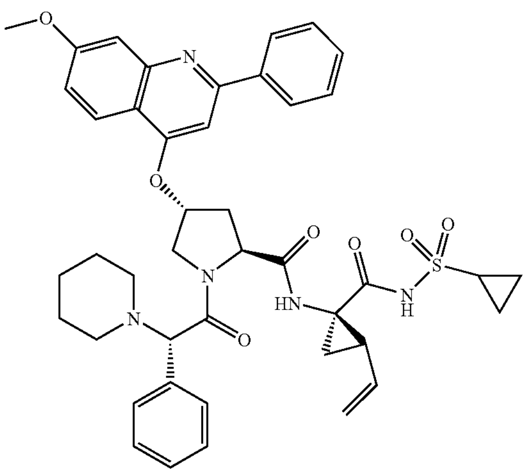 | (2S,4R)-N-((1R,2S)-1-(cyclopropylsulfonylcarbamoyl)-2-vinylcyclopropyl)-4-(7-methoxy-2-phenylquinolin-4-yloxy)-1-((S)-2-phenyl-2-(piperidin-1-yl)acetyl)pyrrolidine-2-carboxamide | ++ |
| 67 | 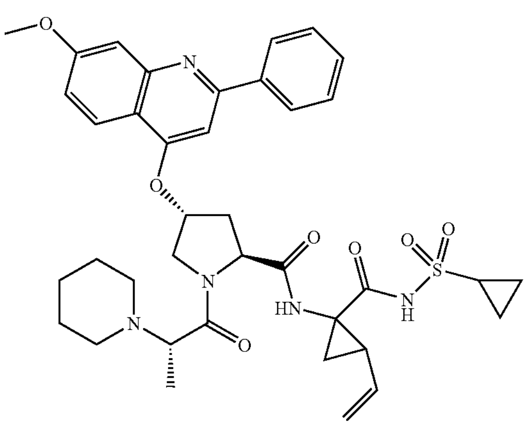 [SMILES: C=CC1CC1(NC(=O)[C@@H]1C[C@@H](Oc2cc(-c3ccccc3)nc3cc(OC)ccc23)CN1C(=O)[C@H](C)N1CCCCC1)C(=O)NS(=O)(=O)C1CC1] | (2S,4R)-N-(1-(cyclopropylsulfonylcarbamoyl)-2-vinylcyclopropyl)-4-(7-methoxy-2-phenylquinolin-4-yloxy)-1-((S)-2-(piperidin-1-yl)propanoyl)pyrrolidine-2-carboxamide | ++ |
| 68 | 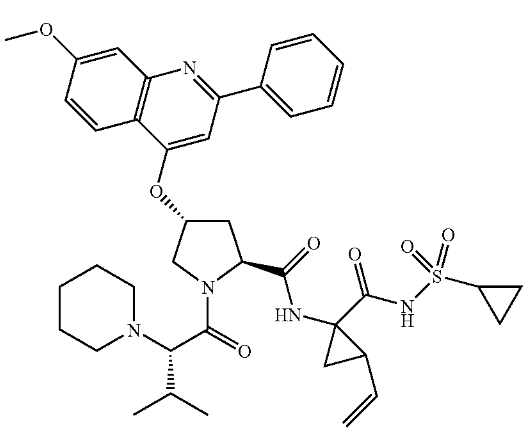 [SMILES: C=CC1CC1(NC(=O)[C@@H]1C[C@@H](Oc2cc(-c3ccccc3)nc3cc(OC)ccc23)CN1C(=O)[C@H](C(C)C)N1CCCCC1)C(=O)NS(=O)(=O)C1CC1] | (2S,4R)-N-(1-(cyclopropylsulfonylcarbamoyl)-2-vinylcyclopropyl)-4-(7-methoxy-2-phenylquinolin-4-yloxy)-1-((S)-3-methyl-2-(piperidin-1-yl)butanoyl)pyrrolidine-2-carboxamide | ++ |

-continued

| Cmp. # | Structure | Name | EC50 |
|---|---|---|---|
| 69 | 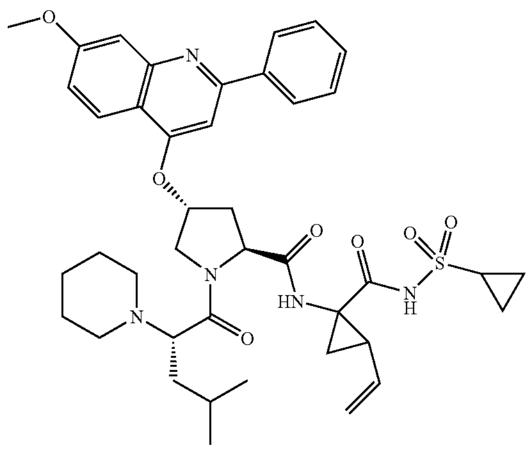 [SMILES: C=CC1CC1(NC(=O)[C@@H]1C[C@@H](Oc2cc(-c3ccccc3)nc3cc(OC)ccc23)CN1C(=O)[C@H](CC(C)C)N1CCCCC1)C(=O)NS(=O)(=O)C1CC1] | (2S,4R)-N-(1-(cyclopropylsulfonylcarbamoyl)-2-vinylcyclopropyl)-4-(7-methoxy-2-phenylquinolin-4-yloxy)-1-((S)-4-methyl-2-(piperidin-1-yl)pentanoyl)pyrrolidine-2-carboxamide | ++ |

Example 6

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.
6A. HCV Replicon and Replicon Expression The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.
6B. Cell Maintenance The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-N1 1, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×$10^5$ cells/10 nil/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

6C. Treatment of HCV-Replicon Containing Cells with Test Compound

HCV replicon-containing cells are rinsed with once PBS once; 2 mls of trypsin are then added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 cells/100 µl/well of 96 well plate (6-7.5×10$^5$ cells/10 ml/plate). Plates are placed into 37° C. 5% $CO_2$ incubator overnight. 6D. Assay The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 µl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 µl of PBS. The PBS is then decanted and the plates tapped in a paper towel to remove any remaining PBS. Cells are fixed in situ with 100 id/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 µl of blocking solution (10% FBS; 3% NGS in PBS) for 30 minutes at room temperature. The blocking solution is removed and 100 µl of rabbit anti-NPTII diluted 1:1000 in blocking solution is added to each well. The plates are then incubated 45-60 minutes at room temperature. After incubation, wells are washed six times with PBS-0.05% Tween-20 solution. 100 µl of 1:15,000 diluted Europium (EU)-conjugated goat anti-rabbit in blocking buffer is added to each well and incubated at room temperature for 30-45 minutes. The plates are washed again and 100 µl of enhancement solution (Perkin Elmer #4001-0010) is added to each well. Each plate is shaken (approx. 30 rpm) in a plate shaker for three minutes. 95 µl is transferred from each well to a black plate; the EU signal is quantitated in a Perkin-Elmer VICTOR plate reader (EU-Lance).

Test Results: Compounds described in the "TABLE OF COMPOUNDS" is Example 5 have been tested in an HCV replication assay, essentially as described in this example.

Example 7

Cytotoxicity Assays

To insure that the decrease in replicon replication is due to compound activity against the HCV replicon rather than non-specific toxicity assays are used to quantitate compound cytotoxicity.

Example 7A

Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

Example 7B

MTS Assay for Cytotoxicity

Cell viability may also be determined by CELLTITER 96 AQUEOUS ONE Solution Cell Proliferation Assay (Promega, Madison Wis.), a colorimetric assay for determining the number of viable cells. In this method, before fixing the cells, 10-20 µl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Album and MTS methods for determining cytotoxicity may be obtained as follows: Cells are treated with different concentrations of test compound or Helioxanthin for a three day-period. Prior to lysis for detection album as described above, the MTS reagent is added according to manufacturer's instruction to each well and incubate at 37° C. and read at OD 490 nm. The cellular album quantitation is then performed as described above.

What is claimed is:

1. A compound or pharmaceutically acceptable salt of the formula

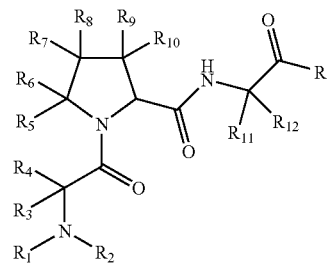

wherein
R is hydroxyl, $C_1$-$C_4$alkoxy,

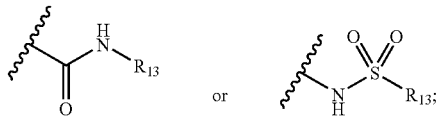

or $R_1$ is, $C_2$-$C_6$alkenyl, $C_3$-$C_7$cycloalkyl, phenyl, heterocycloalkyl, or 5- or 6-membered heteroaryl, each of which is optionally substituted;
$R_2$ is $C_1$-$C_6$ alkyl or $C_2$-$C_6$alkenyl; each of which is optionally substituted; or
$R_1$ and $R_2$ are joined to form a 5- to 7-membered heterocycloalkyl ring, which ring is substituted with 0 or 1 or more substituents independently chosen from halogen, hydroxyl, $C_1$-$C_4$alkyl, $C_1$-$C_4$alkoxy, $C_1$-$C_2$haloalkyl, and $C_1$-$C_2$haloalkoxy;
$R_3$ and $R_{11}$ are independently $C_1$-$C_6$alkyl, $C_2$-$C_6$alkenyl, $C_2$-$C_6$alkanoyl, or mono- or di- $C_1$-$C_6$alkylamino, ($C_3$-$C_7$cycloalkyl)$C_0$-$C_4$alkyl, ($C_3$-$C_7$cycloalkenyl)$C_0$-$C_4$alkyl, (phenyl)$C_0$-$C_2$alkyl, or (heterocycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy,
$R_4$ and $R_{12}$ are independently hydrogen, halogen, hydroxyl, amino, $C_1$-$C_6$alkyl, $C_2$-$C_6$alkenyl, or $C_1$-$C_6$alkoxy; or
$R_3$ and $R_4$ are joined to form a 3- to 7-membered cycloalkyl ring or 5- to 7-membered heterocycloalkyl ring, each of which is substituted with 0 to 2 substituents independently chosen from halogen, hydroxyl, amino, cyano, vinyl, $C_1$-$C_2$alkyl, $C_1$-$C_2$alkoxy, trifluoromethyl, and trifluoromethoxy, or
$R_{11}$ and $R_{12}$ are joined to form a 3- to 7-membered cycloalkyl ring or 5- to 7-membered heterocycloalkyl ring, each of which is substituted with 0 to 2 substituents independently chosen from halogen, hydroxyl, amino, cyano, vinyl, $C_1$-$C_2$alkyl, $C_1$-$C_2$alkoxy, trifluoromethyl, and trifluoromethoxy; or
$R_3$ is a $C_7$-$C_{11}$ saturated or unsaturated hydrocarbon chain that is (i) covalently bound to $R_{11}$, where $R_{11}$ is a methylene group or (ii) covalently bound to a cycloalkyl group formed by $R_{11}$ and $R_{12}$ being joined to form a 3- to 7-membered cycloalkyl ring;
$R_5$ $R_6$, $R_7$, and $R_{10}$ are independently hydrogen, halogen, cyano, amino, hydroxyl, $C_1$-$C_2$alkyl, $C_1$-$C_2$alkoxy, $C_1$-$C_2$haloalkyl, or $C_1$-$C_2$haloalkoxy;
$R_8$ is a group of the formula —$(CH_2)_n$Y—Z, where n is 0, 1, or 2, and
$R_9$ is hydrogen, halogen, amino, $C_1$-$C_2$alkyl, or $C_1$-$C_2$alkoxy; or
$R_8$ and $R_9$ are taken together to form an optionally substituted 5- to 7-membered cycloalkyl ring;
$R_{13}$ is $C_1$-$C_6$alkyl, $C_2$-$C_6$alkenyl, each of which is substituted with 0 or 1 or more substituents independently chosen from halogen, hydroxyl, amino, cyano, amino, $C_1$-$C_4$alkoxy, mono or di-$C_1$-$C_4$alkylamino or
$R_{13}$ is ($C_3$-$C_7$cycloalkyl)$C_0$-$C_2$alkyl, (aryl)$C_0$-$C_2$alkyl, (5- to 7-membered heterocycloalkyl)$C_0$-$C_2$alkyl, or (heteroaryl)$C_0$-$C_2$alkyl, each of which is substituted with 0 or 1 or more substituents independently chosen from halogen, hydroxyl, amino, cyano, amino, $C_1$-$C_4$alkyl, $C_1$-$C_4$alkoxy, mono or di-$C_1$-$C_4$alkylamino, $C_1$-$C_2$haloalkyl, or $C_1$-$C_2$haloalkoxy;
Y is absent, $CR_{14}R_{15}$, $NR_{16}$, S, —O—, —O(C=O)($NR_{16}$)—, —$OC_{14}R_{15}$—, $NH(C=O)(NR_{16})$—, —$NR_{16}$(C=O)$CR_{14}R_{15}$—, $NH(S=O)(NR_{16})$—, or —O(C=O)—; where
$R_{14}$ and $R_{15}$ are independently hydrogen, hydroxyl, halogen, $C_1$-$C_2$alkyl, $C_1$-$C_2$alkoxy, $C_1$-$C_2$haloalkyl, or $C_1$-$C_2$haloalkoxy; and
$R_{16}$ is hydrogen, $C_1$-$C_2$alkyl, $C_1$-$C_2$haloalkyl, or $C_1$-$C_2$haloalkoxy; and
Z is $C_1$-$C_6$alkyl, $C_2$-$C_6$alkenyl, (mono- or bicyclic aryl)$C_0$-$C_2$alkyl, (mono- or bicyclic heteroaryl)$C_0$-$C_2$alkyl, ($C_3$-$C_7$cycloalkyl)$C_0$-$C_2$alkyl, (5- or 6-membered heterocycloalkyl)$C_0$-$C_2$alkyl, partially unsaturated bicyclic heterocycle, tricyclic aryl, or tricyclic hetero aryl;
each of which Z is substituted with 0 or 1 or more substituents independently chosen from halogen, hydroxyl, amino, cyano, —$CONH_2$, —COOH, mono- and di-$C_1$-$C_4$alkylsulfonamide, mono- and di-$C_1$-$C_4$alkylearboxamide, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy, and 0 or 1 ($C_3$-$C_7$cycloalkyl)$C_0$-$C_2$alkyl, (aryl)$C_0$-$C_2$alkyl, (phenyl)$C_0$-$C_2$alkoxy, (5- or 6-membered heteroaryl)$C_0$-$C_2$alkyl, (5- or 6-membered heteroaryl)$C_0$-$C_2$alkoxy, indanyl, (5- or 6-membered heterocycloalkyl)$C_0$-$C_2$alkyl, or 9- or 10 membered bicyclic heteroaryl, each of which is substituted with 0, 1, or 2 substituents independently chosen from (a) and 0 or 1 substituents (b) where:
(a) is chosen from halogen, hydroxyl, amino, cyano, nitro, —COOH, —$CONH_2$, =NOH, $C_1$-$C_4$alkyl, $C_1$-$C_4$alkoxy, $C_2$-$C_4$alkanoyl, $C_1$-$C_4$hydroxyalkyl, mono- and di-$C_1$-$C_4$alkylamino, $C_1$-$C_4$alkylester, mono- or di- $C_1$-$C_4$alkylsulfonamide, mono- and di-$C_1$-$C_4$alkylearboxamide, $C_1$-$C_2$haloalkyl, $C_1$-$C_2$haloalkoxy, and
(b) is phenyl and 5- or 6-membered heteroaryl, each of which is substituted with 0 or 1 or more substituents independently chosen from halogen, hydroxyl, amino, —CHO, —COOH, —NH(C=O)H, $C_1$-$C_4$alkyl, $C_1$-$C_2$alkoxy, mono- and di-($C_1$-$C_4$alkyl)amino, mono- and di-($C_1$-$C_4$alkyl)carboxamide, $C_1$-$C_4$alkylester, ($C_1$-$C_4$alkylester)amino, $C_1$-$C_2$haloalkyl, and $C_1$-$C_2$haloalkoxy.

2. A compound or salt of claim 1, in which
$R_1$ and $R_2$ are joined to form a pyrrolidinyl, piperidinyl, or piperazinyl ring, each of which is substituted with 0, 1, or 2 substituents independently chosen from halogen, hydroxyl, $C_1$-$C_2$alkyl, $C_1$-$C_2$alkoxy, trifluoromethyl, and trifluoromethoxy.

3. A compound or salt of claim 1, in which:
$R_3$ is $C_1$-$C_6$alkyl, $C_2$-$C_6$alkenyl, $C_2$-$C_6$alkanoyl, or mono- or di- $C_1$-$C_6$alkylamino, ($C_3$-$C_7$cycloalkyl)$C_0$-$C_4$alkyl, ($C_3$-$C_7$cycloalkenyl)$C_0$-$C_4$alkyl, (phenyl)$C_0$-$C_2$alkyl, or (heterocycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy, and
$R_4$ is hydrogen, $C_1$-$C_6$alkyl, $C_2$-$C_6$alkenyl, or $C_1$-$C_6$alkoxy.

4. A compound or salt of claim 1 in which $R_3$ and $R_4$ are joined to form a cyclopropyl ring, which is substituted with 0 to 2 substituents independently chosen from vinyl, $C_1$-$C_2$alkyl, and $C_1$-$C_2$alkoxy.

5. A compound or salt of claim 1, in which:

$R_{11}$ is $C_1$-$C_6$alkyl, $C_2$-$C_6$alkenyl, $C_2$-$C_6$alkanoyl, or mono- or di- $C_1$-$C_6$alkylamino, ($C_3$-$C_7$cycloalkyl)$C_0$-$C_4$alkyl, ($C_3$-$C_7$cycloalkenyl)$C_0$-$C_4$alkyl, (phenyl)$C_0$-$C_2$alkyl, or (heterocycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy, and $R_{12}$ is hydrogen, $C_1$-$C_6$alkyl, $C_2$-$C_6$alkenyl, or $C_1$-$C_6$alkoxy.

6. A compound or salt of claim 1 in which $R_3$ and $R_4$ are joined to form a cyclopropyl ring, which is substituted with 0 to 2 substituents independently chosen from vinyl, $C_1$-$C_2$alkyl, and $C_1$-$C_2$alkoxy.

7. A compound or salt of claim 1 of the formula

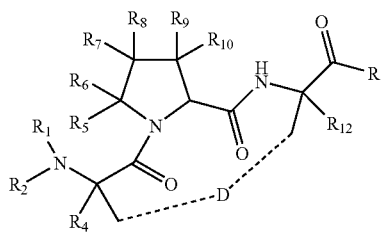

where D is an alkyl or alkenyl group having 6 to 10 carbon atoms.

8. A compound or salt of claim 7 of the formula

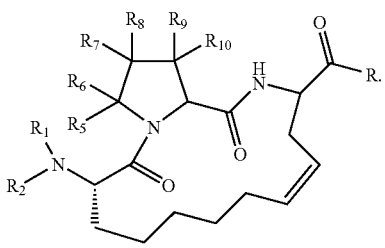

9. A compound or salt of claim 1 of the formula

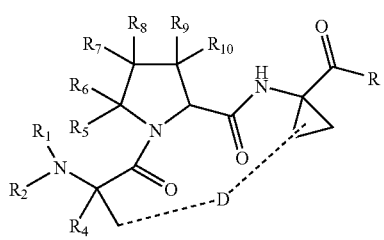

where D is an alkyl or alkenyl group having 6 to 10 carbon atoms.

10. A compound or salt of claim 9 of the formula

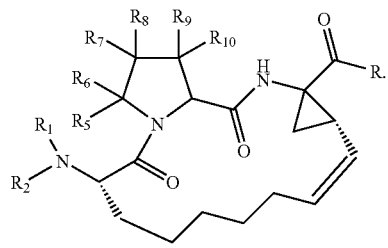

11. A compound or salt of claim 1, in which $R_5$ $R_6$, $R_7$, and $R_{10}$ are all hydrogen.

12. A compound or salt of claim 1, in which $R_8$ is a group of the formula —$(CH_2)_n$Y—Z, where n is 0, 1, or 2, and $R_9$ is hydrogen, halogen, amino, $C_1$-$C_2$alkyl, or $C_1$-$C_2$alkoxy.

13. A compound or salt of claim 12 in which n is 0 and Y is —O— or —O(C=O)—.

14. A compound or salt of claim 1, wherein

Z is a group of the formula

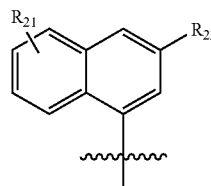 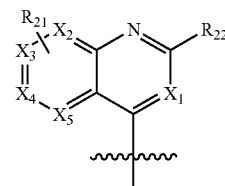

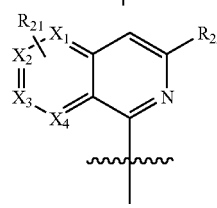 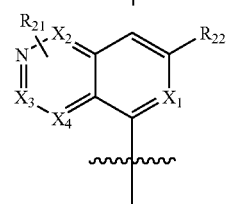

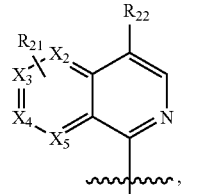 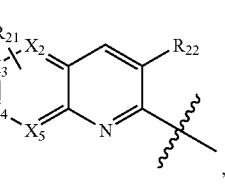

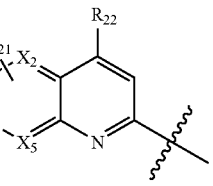 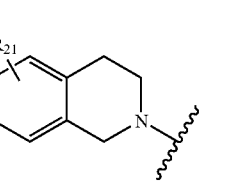 or

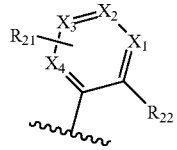

wherein $X_1$, $X_2$, $X_3$, and $X_4$, are independently N or CH and no more than two of $X_1$-$X_4$ are N;

$R_{21}$ represents from 0 to 3 groups independently chosen from halogen, hydroxyl, amino, cyano, —CONH$_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

$R_{22}$ is hydrogen, halogen, hydroxyl, amino, cyano, —CONH$_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy, or $R_{22}$ is ($C_3$-$C_7$cycloalkyl)$C_0$$C_2$alkyl, (phenyl)$C_0$$C_2$alkyl, (phenyl)$C_0$$C_2$alkoxy, (5- or 6-membered heteroaryl)$C_0$-$C_2$alkyl, (5- or 6-membered heteroaryl)$C_0$-$C_2$alkoxy, indanyl, (5- or 6-membered heterocycloalkyl)$C_0$$C_2$alkyl, or 9- or 10 membered bicyclic heteroaryl, each of which is substituted with 0, 1, or 2 substituents independently chosen from (a) and 0 or 1 substituents (b) where (a) is chosen from halogen, hydroxyl, amino, cyano, nitro, —COOH, —CONH$_2$, CH$_3$(C=O)NH—, $C_1$-$C_4$alkyl, $C_1$-$C_4$alkoxy, $C_1$-$C_4$hydroxyalkyl, mono- and di-$C_1$-$C_4$alkylamino, $C_1$-$C_4$alkylester, mono- and di- $C_1$-$C_4$alkylsulfonamide, mono- and di-$C_1$-$C_4$alkylcarboxamide, $C_1$-$C_2$haloalkyl, and $C_1$-$C_2$haloalkoxy, and (b) is phenyl or 5- or 6-membered heteroaryl, each of which is substituted with 0 or 1 or more of halogen, hydroxyl, $C_1$-$C_4$alkyl, and $C_1$-$C_2$alkoxy.

15. A compound or salt of claim 1 of the formula

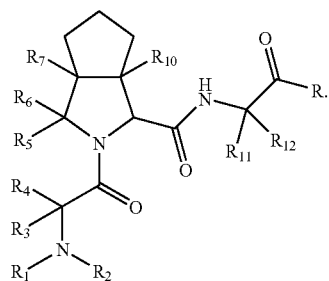

16. A compound or salt of claim 15 wherein $R_3$ is $C_1$-$C_6$alkyl, ($C_3$-$C_7$cycloalkyl)$C_0$-$C_4$alkyl, or (phenyl)$C_0$-$C_2$alkyl, each of which is substituted with 0 to 3 substituents independently chosen from halogen, hydroxyl, $C_1$-$C_2$alkyl, $C_1$-$C_2$alkoxy, mono- and di-$C_1$-$C_2$alkylamino, $C_1$-$C_2$haloalkyl, and $C_1$-$C_2$haloalkoxy; and $R_4$ is hydrogen, $C_1$-$C_2$alkyl, or $C_1$-$C_2$alkoxy; or $R_3$ and $R_4$ are joined to form a cyclopropyl ring, which is substituted with 0 to 2 substituents independently chosen from vinyl, $C_1$-$C_2$alkyl, and $C_1$-$C_2$alkoxy;

$R_{11}$ is $C_1$-$C_6$alkyl, ($C_3$-$C_7$cycloalkyl)$C_0$-$C_4$alkyl, or (phenyl)$C_0$-$C_2$alkyl, each of which is substituted with 0 to 3 substituents independently chosen from halogen, hydroxyl, $C_1$-$C_2$alkyl, $C_1$-$C_2$alkoxy, mono- and di-$C_1$-$C_2$alkylamino, $C_1$-$C_2$haloalkyl, and $C_1$-$C_2$haloalkoxy; and $R_{12}$ is hydrogen, $C_1$-$C_2$alkyl, or $C_1$-$C_2$alkoxy; or $R_{11}$ and $R_{12}$ are joined to form a cyclopropyl ring, which is substituted with 0 to 2 substituents independently chosen from vinyl, $C_1$-$C_2$alkyl, and $C_1$-$C_2$alkoxy; and $R_5$, $R_6$, $R_7$, and $R_{10}$ are each independently hydrogen, methyl or methoxy.

17. A compound or salt of claim 15 of the formula

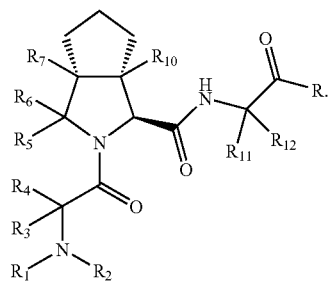

18. A compound or salt of claim 15 of the formula

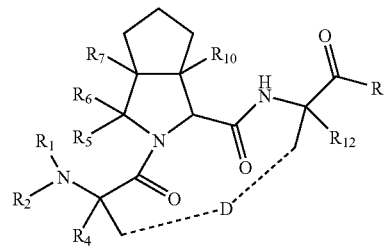

where D is an alkyl or alkenyl group having 6 to 10 carbon atoms;
$R_4$ and $R_{12}$ are independently hydrogen or methyl; and
$R_5$, $R_6$, $R_7$, and $R_{10}$ are independently hydrogen or methyl.

19. A compound or salt of claim 15 of the formula

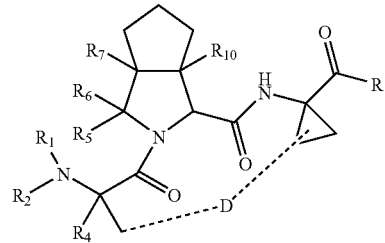

where D is an alkyl or alkenyl group having 6 to 10 carbon atoms;
$R_4$ and $R_{12}$ are independently hydrogen or methyl; and
$R_5$, $R_6$, $R_7$, and $R_{10}$ are independently hydrogen or methyl.

20. A pharmaceutical composition comprising a compound or salt of claim 1, containing at least one pharmaceutically acceptable carrier.

21. A method for treating hepatitis C infection in a subject having hepatitis C infection comprising providing an effective amount of a compound or salt of claim 1 to a patient in need of such treatment.

22. A compound or salt of claim 1, wherein the compound is

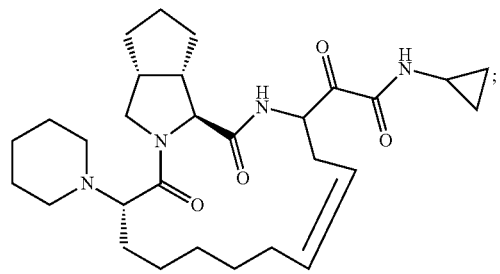 [SMILES: O=C(NC1CC1)C(=O)C1C/C=C\CCCCC[C@H](N2CCCCC2)C(=O)N2C[C@@H]3CCC[C@@H]3[C@H]2C(=O)N1]

N-(1-(cyclopropylamino)-1,2-dioxohexan-3-yl)-2-(2-(piperidin-1-yl)propanoyl) octahydrocyclopenta[c]pyrrole-1-carboxamide;

N-(1-(cyclopropylamino)-1,2-dioxohexan-3-yl)-2-(2-phenyl-2-(piperidin-1-yl)acetyl) octahydrocyclopenta[c]pyrrole-1-carboxamide;

2-(2-(azepan-1-yl)propanoyl)-N-(1-(cyclopropylamino)-1,2-dioxohexan-3-yl) octahydrocyclopenta[c]pyrrole-1-carboxamide;

tert-butyl (2S)-1-(1-(1-(cyclopropylamino)-1,2-dioxohexan-3-ylcarbamoyl) hexahydrocyclopenta[c]pyrrol-2(1H)-yl)-3,3-dimethyl-1-oxobutan-2-ylcarbamate;

N-(1-(cyclopropylamino)-1,2-dioxohexan-3-yl)-2-(2-(pyrrolidin-1-yl)propanoyl) octahydrocyclopenta[c]pyrrole-1-carboxamide;

tert-butyl 4-(1-(1-(1-(cyclopropylamino)-1,2-dioxohexan-3-ylcarbamoyl) hexahydrocyclopenta[c]pyrrol-2(1H)-yl)-1-oxopropan-2-yl)piperazine-1-carboxylate;

N-(1-(cyclopropylamino)-1,2-dioxohexan-3-yl)-2-((R)-2-(piperidin-1-yl)propanoyl) octahydrocyclopenta[c]pyrrole-1-carboxamide;

N-(1-(cyclopropylamino)-1,2-dioxohexan-3-yl)-2-((R)-2-(pyrrolidin-1-yl)propanoyl) octahydrocyclopenta[c]pyrrole-1-carboxamide;

(3R,5S)-5-(1-(cyclopropylamino)-1,2-dioxohexan-3-ylcarbamoyl)-1-(2-(piperidin-1-yl)propanoyl)pyrrolidin-3-yl 3,4-dihydroisoquinoline-2(1H)-carboxylate;

(3R,5S)-5-(1-(cyclopropylamino)-1,2-dioxohexan-3-ylcarbamoyl)-1-(2-(pyrrolidin-1-yl)propanoyl)pyrrolidin-3-yl 3,4-dihydroisoquinoline-2(1H)-carboxylate;

N-(1-(cyclopropylamino)-1,2-dioxohexan-3-yl)-2-((S)-2-(piperidin-1-yl)propanoyl) octahydrocyclopenta[c]pyrrole-1-carboxamide;

N-(1-(cyclopropylamino)-1,2-dioxohexan-3-yl)-2-((S)-3,3-dimethyl-2-(piperidin-1-yl)butanoyl) octahydrocyclopenta[c]pyrrole-1-carboxamide;

N-(1-(cyclopropylamino)-1,2-dioxohexan-3-yl)-2-((S)-3,3-dimethyl-2-(piperidin-1-yl)butanoyl)octahydrocyclopenta[c]pyrrole-1-carboxamide;

N-(1-(cyclopropylamino)-1,2-dioxohexan-3-yl)-2-((S)-3-methyl-2-(piperidin-1-yl)butanoyl) octahydrocyclopenta[c]pyrrole-1-carboxamide;

ethyl 1-((2S,4R)-1-((S)-3,3-dimethyl-2-(piperidin-1-yl)butanoyl)-4-(7-methoxy-2-phenylquinolin-4-yloxy)pyrrolidine-2-carboxamido)-2-vinylcyclopropanecarboxylate;

ethyl 1-((2S,4R)-4-(7-methoxy-2-phenylquinolin-4-yloxy)-1((S)-2-phenyl-2-(piperidin-1-yl)acetyl)pyrrolidine-2-carboxamido)-2-vinylcyclopropanecarboxylate;

ethyl 1-((2S,4R)-4-(7-methoxy-2-phenylquinolin-4-yloxy)-1((S)-3-methyl-2-(piperidin-1-yl)butanoyl)pyrrolidine-2-carboxamido)-2-vinylcyclopropanecarboxylate;

ethyl 1-((2S,4R)-1((S)-2-cyclohexyl-2-(piperidin-1-yl)acetyl)-4-(7-methoxy-2-phenylquinolin-4-yloxy)pyrrolidine-2-carboxamido)-2-vinylcyclopropanecarboxylate;

ethyl 1-((2S,4R)-4-(7-methoxy-2-phenylquinolin-4-yloxy)-1-((S)-2-(piperidin-1-yl)propanoyl)pyrrolidine-2-carboxamido)-2-vinylcyclopropanecarboxylate;

1-((2S,4R)-1((S)-3,3-dimethyl-2-(piperidin-1-yl)butanoyl)-4-(7-methoxy-2-phenylquinolin-4-yloxy)pyrrolidine-2-carboxamido)-2-vinylcyclopropanecarboxylic acid;

1-((2S,4R)-4-(7-methoxy-2-phenylquinolin-4-yloxy)-1((S)-2-phenyl-2-(piperidin-1-yl)acetyl)pyrrolidine-2-carboxamido)-2-vinylcyclopropanecarboxylic acid;

1-((2S,4R)-4-(7-methoxy-2-phenylquinolin-4-yloxy)-1((S)-3-methyl-2-(piperidin-1-yl)butanoyl)pyrrolidine-2-carboxamido)-2-vinylcyclopropanecarboxylic acid;

1-((2 S,4R)-1-((S)-2-cyclohexyl-2-(piperidin-1-yl)acetyl)-4-(7-methoxy-2-phenylquinolin-4-yloxy)pyrrolidine-2-carboxamido)-2-vinylcyclopropanecarboxylic acid;

1-((2S,4R)-4-(7-methoxy-2-phenylquinolin-4-yloxy)-1-((S)-2-(piperidin-1-yl)propanoyl)pyrrolidine-2-carboxamido)-2-vinylcyclopropanecarboxylic acid;

(2R,6S,16aS,Z)-ethyl 2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate;

(2R,6S,16aS,Z)-2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid;

(2R,6S,13aR,14aS,16aS,Z)-ethyl 2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4]diazacyclopentadecine-14a-carboxylate;

(2R,6S,13aS,14aR,16aS,Z)-ethyl 2-(7-methoxy-2-phenylquinolin-4-yloxy)-5,16-dioxo-6-(piperidin-1-yl)-1,2,3,5,6,7,8,9,10,11,13a,14,14a,15,16,16a-hexadecahydrocyclopropa[e]pyrrolo[1,2-a][1,4] diazacyclopentadecine-14a-carboxylate;

(2S,4R)-1-((S)-2-cyclohexyl-2-(piperidin-1-yl)acetyl)-N-(1-(cyclopropylsulfonylcarbamoyl)-2-vinylcyclopropyl)-4-(7-methoxy-2-phenylquinolin-4-yloxy)pyrrolidine-2-carboxamide;

(2S,4R)-N-((1S ,2R)-1-(cyclopropylsulfonylcarbamoyl)-2-vinylcyclopropyl)-4-(7-methoxy-2-phenylquinolin-4-yloxy)-1-((S)-2-phenyl-2-(piperidin-1-yl)acetyl)pyrrolidine-2-carboxamide;

(2S,4R)-N-((1R,2 S)-1-(cyclopropylsulfonylcarbamoyl)-2-vinylcyclopropyl)-4-(7-methoxy-2-phenylquinolin-4-yloxy)-1-((S)-2-phenyl-2-(piperidin-1-yl)acetyl)pyrrolidine-2-carboxamide;

(2S,4R)-N-(1-(cyclopropylsulfonylcarbamoyl)-2-vinylcyclopropyl)-4-(7-methoxy-2-phenylquinolin-4-yloxy)-1-((S)-2-(piperidin-1-yl)propanoyl)pyrrolidine-2-carboxamide;

(2S,4R)-N-(1-(cyclopropylsulfonylcarbamoyl)-2-vinylcyclopropyl)-4-(7-methoxy-2-phenylquinolin-4-yloxy)-1-((S)-3-methyl-2-(piperidin-1-yl)butanoylpyrrolidine-2-carboxamide; or (2S,4R)-N-(1-(cyclopropylsulfonylcarbamoyl)-2-vinylcyclopropyl)-4-(7-methoxy-2-phenylquinolin-4-yloxy)-1-((S)-4-methyl-2-(piperidin-1-yl)pentanoyl)pyrrolidine-2-carboxamide.

* * * * *